(12) United States Patent
McGimpsey

(10) Patent No.: US 6,902,720 B2
(45) Date of Patent: Jun. 7, 2005

(54) CYCLIC PEPTIDE STRUCTURES FOR MOLECULAR SCALE ELECTRONIC AND PHOTONIC DEVICES

(75) Inventor: William Grant McGimpsey, Boylston, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 10/143,733

(22) Filed: May 10, 2002

(65) Prior Publication Data

US 2003/0144185 A1 Jul. 31, 2003

Related U.S. Application Data

(60) Provisional application No. 60/289,972, filed on May 10, 2001.

(51) Int. Cl.$^7$ ................................................. A61L 9/04
(52) U.S. Cl. .......................... 424/45; 530/321; 530/323; 514/9; 930/270
(58) Field of Search .......................... 424/45; 930/270; 514/9; 530/321, 323

(56) References Cited

U.S. PATENT DOCUMENTS

| | | |
|---|---|---|
| 4,877,501 A | 10/1989 | Schnur et al. |
| 4,990,291 A | 2/1991 | Schoen et al. |
| 5,876,748 A | 3/1999 | Shimizu et al. |
| 5,922,214 A | 7/1999 | Liu et al. |
| 5,965,258 A | 10/1999 | Riess et al. |
| 6,013,206 A | 1/2000 | Price et al. |
| 6,322,713 B1 | 11/2001 | Choi et al. |

OTHER PUBLICATIONS

C.H. Hassall, "Some Studies Relating to the Synthesis of Cylindrical Peptides", Chemistry and Biology of Peptides, Proc. 3rd American Peptide Symposium, ed. J.Meinhoffer, Ann Arbor Science (Ann Arbor, MI 1972), p 153–157.

(Continued)

*Primary Examiner*—Christopher R. Tate
*Assistant Examiner*—B. Dell Chism
(74) *Attorney, Agent, or Firm*—R. Dennis Greenlan, Esq.

(57) ABSTRACT

The present invention discloses a family of cyclic peptide monomers and supramolecular cyclic peptide structures comprising chromophore residues which possess electronic and electro-optic properties for producing molecular scale electronic and photonic devices made from such materials. More particularly, this invention provides for cyclic peptide nanotube structures formed from a plurality of stacked cyclic peptides comprising chromophore residues that provide molecular scale electronic conductivity and non linear optical behavior. The stackable cyclic peptide is represented by the general formula

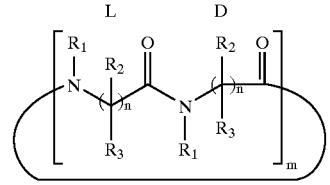

where $R_1$ is H, $CH_3$ or alkyl; where at least one $R_2$ is a chromophore; where $R_3$ is H, $CH_3$ or a polar or non-polar organic functional group used for controlling peptide stacking and solubility; where n equals 1 or 2; where m equals 4 or 6; and where a first adjacent amino acid residue has an α-carbon chirality of L and a second adjacent amino acid residue has an α-carbon chirality of D.

1 Claim, 19 Drawing Sheets

OTHER PUBLICATIONS

I.L. Karle et al., "The Conformation of the Cyclic Tetrapeptide L–Ser(O–t–Bu)–beta–Ala–Gyl–L–beta–Asp(OMe) Containing a 14–Membered Ring", Acta Cryst., B31:555–560 (1975).

L. Tomasic et al., "Some Cyclic Oligopeptides with S–2n Symmetry", Helvetica Chemica Acta, 70:1012–1016 (1987).

V. Pavone et al. "Regularly Alternating L,D–Peptides. III. Hexacylclic Peptides from Valine or Phenylalanine", Biopolymers, 28:215–223 (1989).

M.R. Ghadiri et al., "Self–assembling organinc nanotubes based on a cyclic peptide architecture", Nature, 366, Nov. 25, 1993, p 325–327.

N. Khazanovich et al., Nanoscale Tubular Ensembles with Specified Internal Diameters, J.Am.Chem.Soc., 116:6011–6012 (1994).

M. Engels et al., "Structure and Dynamics of Self–Assembling Peptide Nanotubes and the Channel–Mediated Water Organization and Self–Diffusion", J.Am.Chem.Soc., 117:9151–9158 (1995).

T.D. Clark, "Supramolecular Design by Covalent Capture. Design of a Peptide Cylinder via Hydrogen–Bond–Promoted Intermolecular Olefin Metathesis", J.Am.Chem.Soc., 117:12364–12365 (1995).

M.R. Ghadiri, "Self–Assembled Nanoscale Tubular Ensembles", Adv. Mater. 7(7):675–677 (1995).

M.R. Ghadiri et al., "The Structural and Thermodynamic Basis for the Formation of Self–Assembled Peptide Nanotubes", Angew.Chem.Int.Ed.Engl., 34(1):93–95 (1995).

J.D. Hartgerink et al., "Self–Assembling Peptide Nanotubes", J.Am.Chem.Soc., 118:43–50 (1996).

D.H. Lee et al., "A self–replicating peptide", Nature, vol. 382, Aug. 8, 1996, p 525–528.

K. Motesharei et al., "Diffusion–Limited Size–Selective Ion Sensing Based on SAM–Supported Peptide Nanotubes", J.Am.Chem.Soc., 119:11306–11312 (1997).

J.M. Buriak et al., "Self–assembly of peptide based nanotubes", Mat. Sci. Eng. C4:207–212 (1997).

D. Seeback et al., "Cyclo–beta–peptides:Structure and Tubular Stacking of Cyclic Tetramers of 3–Aminobutanoic Acid as Determined from Powder Diffraction Data", Helvetica Chimica Acta, 80:173–182 (1997).

H. Mihara et al., "A pair of pyrene groups as a conformational probe for antiparallel beta–sheet structure formed in cyclic peptides", J.Chem.Soc. Perkin Trans. 2:517–522 (1997).

T.D. Clark et al., "Self–Assembling Cyclic beta3–Peptide Nanotubes as Artificial Transmembrane Ion Channels", J.Am.Chem.Soc., 120:651–656 (1998).

H.S. Kim et al., "Oriented Self–Assembly of Cyclic Peptide Nanotubes in Lipid Membranes", J.Am.Chem.Soc., 120:4417–4424 (1998).

J.D. Hartgerink et al., "Peptide Nanotubes and Beyond", Chem.Eur.J., 4(8):1367–1372 (1998).

C. Steinem et al., "Reversible Photoisomerization of Self–Organized Cylindrical Peptide Assemblies at Air–Water and Solid Interfaces", Langmuir, 15:3956–3964 (1999).

M.S. Vollmer et al., "Photoswitchable Hydrogen–Bonding in Self–Organizaed Cylindrical Peptide Systems", Angew.Chem.Int.Ed., 38(11):1598–1601 (1999).

J.D. Hartgerink et al., "Self–Assembly and Mineralization of Peptide–Amphiphile Nanofibers", Science, vol. 294, Nov. 23, 2001, p 1684–1688.

CYCLIC PEPTIDE STRUCTURES FOR MOLECULAR SCALE ELECTRONIC AND PHOTONIC DEVICES

CROSS-REFERENCES

This application claims the benefit under 35 U.S.C. 119(e) of co-pending U.S. provisional patent application U.S. Ser. No. 60/289,972 filed on May, 10, 2001 which is RECEIVED incorporated herein by this reference.

FIELD OF THE INVENTION

This invention relates to cyclic peptide monomers and supramolecular cyclic peptide structures comprising chromophore residues which possess electronic and electro-optic properties and molecular scale electronic and photonic devices made from such materials. More particularly, this invention relates to cyclic peptide nanotube structures formed from a plurality of stacked cyclic peptides comprising chromophore residues that provide molecular scale electronic conductivity and non linear optical behavior.

BACKGROUND OF THE INVENTION

With the growing need to downsize devices, scientists have been attempting to construct molecular scale devices, which perform applications similar to those of their macroscopic counterparts. To this end, we would like to design systems (either molecular or supramolecular) that promote efficient and controllable charge or energy transfer. Cyclic peptides offer an excellent scaffold for the construction of such systems, as they readily self-assemble into peptide nanotubes. Through selective chromophore substitution on these cyclic-peptides, long range energy and/or charge transfer can occur, which allows the nanotube system to function like a molecular scale wire. To date, we have focused on the novel synthesis of cyclic peptides containing pyrene. While these systems will likely undergo long-range transfer, they will also serve as a diagnostic for the nature of cyclic peptide self-assembly, due to the unique photochemistry of pyrene.

Since 1959, the number of devices on an integrated circuit chip has increased from 1 to 10 million. As a result there is an increasing demand for nanoscale materials with new electronic, chemical and physical properties. Nanotubes are of special interest for different utilities, for example, containment of nanowires, optical and electronic devices, catalytic media, therapeutic agents, trans-membrane channels and drug delivery vehicles. Carbon graphite nanotubes, boron nitride nanotubes, zeolites, and crown ether based tubes are well-known nanostructures.

In 1993, self-assembling cyclic D, L-peptides were observed as hollow tubular structures by electron microscopy, electron diffraction, FT-W, and molecular modeling. Cyclic peptides with an even number of alternating D-, L-amino acids preferentially adopt flat disk like conformations in which all backbone amide functionalities lie approximately perpendicular to the plain of the structure. In this confirmation, subunits can stack in an anti-parallel fashion and participate in backbone—backbone intermolecular hydrogen bonding to produce a contiguous n-sheet structure. Moreover, because of the D- and L-amino acids sequence, peptide side chains must necessarily lie on the outside of the ensemble thereby resulting in the desired hollow tubular structure. When protonated, cyclic polypeptides crystallize into tubular structures hundreds of nanometer long, with internal diameters of 7–8 Å. We are making cyclic peptides with different amino acids that have two different chromophore groups on one cycle. Nowadays, we are focused on the difference between the cyclic peptides that make dimer stacking, non-stacking and stacking in terms of energy transfer between the chromophores.

SUMMARY OF THE INVENTION

The present invention pertains to the fabrication of molecular scale devices that may be useful in nanoscale electronics and photonics applications. Specific applications of the devices may include replacements for conventional wires, switches and other electronics components that are particularly useful for performing logic operations and data storage, as well as non-linear optical devices. The present invention pertains to the fabrication of supramolccular cyclic peptide assemblies from individual cyclic peptide molecules which themselves have been synthesized from unnatural amino acid building blocks. These assemblies can function in place of conventional macroscopic electronic devices such as, but not limited to, wires and switches. The function of these devices relies on the controlled and predictable flow of charge or excitation energy within the supramolecular assembly. This can be achieved by incorporating appropriate thermodynamic gradients into the assembly. It is anticipated that these peptide assemblies, when linked with other structures by appropriate covalent bonds, will provide enabling technology for the construction of molecular logic circuits and molecular scale data storage. These assemblies may also exhibit non-linear optical behavior.

The invention is based on the efficient and controlled flow of charge or excitation energy within the supramolecular assembly. Ample precedent for such behavior is provided by numerous reported studies of intra- and inter-molecular electron, hole and energy transfer. Electron transfer and singlet-singlet and triplet-triplet energy transfer occurs in solution and in the solid state between donors and acceptors when the transfer process is exothermic, that is when there is a downhill energy gradient for the transfer. These transfer processes occur in solution at diffusion controlled rates over distances of up to 10 nm. In large polychromophoric molecules, charge transfer and singlet-singlet and triplet-triplet energy transfer have been shown to occur between individual chromophores in the same molecule at rates exceeding $10^{10}$ $s^-$. Additionally, antenna effects in polymers containing light absorbing and other chromophores demonstrate the feasibility of long range transfer of excitation energy by way of singlet and triplet excitons. Where the term "chromophore" is used herein it refers to rigid and flat extended, conjugated π systems other than benzene having at least two aromatic rings which are preferably fused aromatic rings as well as other systems such as porphorins and pthalocyanines.

BRIEF DESCRIPTION OF THE DRAWINGS

This invention is pointed out with particularity in the appended claims. Other features and benefits of the invention can be more clearly understood with reference to the specification and the accompanying drawings in which:

DESCRIPTION OF THE PREFERRED EMBODIMENTS

The present invention describes a nanometer scale electronic device fabricated by the self-assembly of cyclic peptide nanotubes. Peptides are single molecules consisting of a chain of amino acids that are covalently linked via an amide or peptide bond. A cyclic peptide is created by linking together the two terminal amino acids in the chain by a similar amide bond. In certain environments, the hydrogen-bonding sites on the amino acids facilitate the assembly of individual cyclic peptide molecules into rigid linear stacks. The resulting structure has been referred to as a nanotube since the supramolecular assembly resembles a pipe or tube. The nanotube structure is stabilized by intermolecular hydrogen bonds and is remarkably rugged. Harsh conditions, such as refluxing in strong acid, are required to disrupt the structure. Under milder conditions the structure is stable for indefinite periods and can be crystallized and imaged with various electron and tunneling microscopes.

The present invention utilizes the well-defined, rigid, linear supramolecular structure of a cyclic peptide nanotube as a molecular scaffold or superstructure which physically supports but does not directly participate in anticipated device operation. Rather, some or all of the amino acids that compose the cyclic peptide are modified to contain functional groups that facilitate device function. The invention described below deals primarily with the fabrication of a molecular wire, although it will be understood by those skilled in the art of molecular device design that altering the identity of the added functional groups will provide for other forms of device operation.

Preferred Cyclic Peptide Structures

Figure 1:
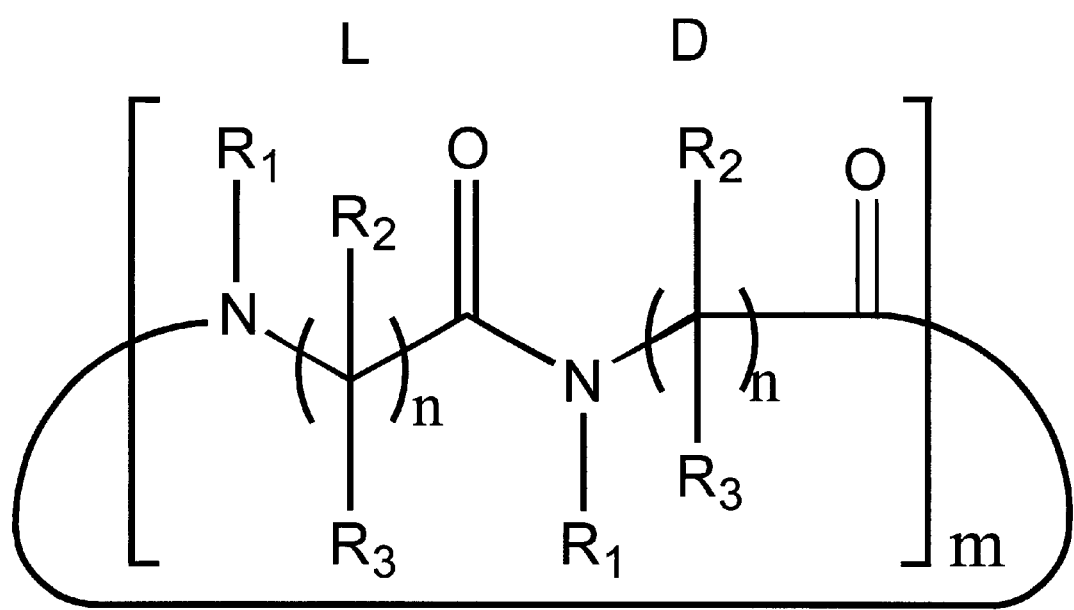
FIG. 1 show the basic repetitive unit of the cyclic peptide structure of the present invention.

The basic building block of the stackable cyclic peptide of the present invention is shown in FIG. 1. In this figure and FIGS. 2, 3, 4, 5, 6, 7 and 8, the chirality denoted is for the alpha carbon. Beta amino acids and those amino acids with longer carbon chains may have additional, different chirality as long as nanotubes can still be formed. It is not clear at this point what combinations of chiral centers in beta and longer chain analogs will lead to stacking. In a typical application, alpha or beta amino acids may be employed where n equals 1 for alpha amino acid residues and n equals 2 for beta amino acid residues. In other embodiments, where non-naturally occurring amino acid residues are employed, n may be greater than 2.

The structure shown in FIG. 1 represents a general structure of a cyclic peptide that is typically employed with the present invention. Similar structures may also be employed. In the example structure shown in FIG. 1, the N-terminus is placed to the left and the C-terminus is place to the right with the L- and D-chirality on the left and right amino acid residue, respectively. It is important to note that this is an arbitrary representation in terms of the order of chirality and in terms of the order of the termini and that the chirality and termini may be reversed.

Several features shown in FIG. 1 are worth noting. The structure shown in FIG. 1 consists of a sequence of amino acid residues that are coupled by peptide bonds. The basic unit consists of one amino acid with L-chirality and one amino acid with D-chirality. The basic unit is repeated "m" times where m>0 and, in example embodiments provided below, m is shown equal to 4 or 6 although other values for m are possible in other embodiments. The terminal amino acids in the sequence are coupled to each other through a peptide bond to produce a cyclic molecule. It should be noted that alternating chirality is necessary for the cyclic peptide monomers to stack into nanotubes.

As shown in FIG. 1, the amino acid residues are either α or β, meaning that they contain either one carbon atom between the carboxyl carbon and the nitrogen atom in the backbone (n=1) or they contain two carbon atoms between the carboxyl carbon and the nitrogen atom (n=2). In the case of β amino acids, the substituents R2 and R3 refer to substituents on the α-carbon, i.e., the carbon adjacent to the carboxyl group. Usually the substituents on the β-carbon will be H and H. However, if other substituents are used, they are chosen such that the structure produced will still be capable of stacking into nanotubes. In FIG. 1, the $R_1$, $R_2$ and $R_3$ groups have the following potential identities:

(a) $R_1$ is either H, $CH_3$ or an alkyl. Here, the natural amino acids have $R_1$=H. If it is desirable to limit the amount of nanotube stacking, $CH_3$ or alkyl can be used;

(b) $R_2$ is either a side chain found in natural amino acids, or a chromophore side chain that is necessary for providing the device function described in the invention, or a side chain that is necessary to allow a bond to be formed between the cyclic peptides or cyclic peptide nanotubes and a surface, for example, gold, silver, silicon or silica; and (c) $R_3$ is H, $CH_3$, or other organic functional groups that can be used to control nanotube formation and solubility.

The identity of the $R_2$ Groups are varied. There are 20 naturally-occurring amino acids all of which can be used in this invention and all of which have different identities for $R_2$. These amino acids are: Glycine, Alanine, Valine, Leucine, Isoleucine, Methionine, Proline, Phenylalanine, Tryptophan, Serine, Threonine, Asparagine, Glutamine, Tyrosine, Cysteine, Lysine, Arginine, Histidine, Arpartic Acid, Glutamic Acid. Table 1 lists the corresponding side chains for each of the naturally-occurring amino acids. In addition there are $R_2$ groups which are chromophores that are necessary for the functioning of the invention. These groups can be attached at the α or β carbon atoms of the amino acids but for the sake of simplicity here are always attached at the α-carbon atom of the amino acid. Furthermore, the linking group between the α-carbon and the chromophore group can be a variety of groups including alkyl groups and alkyl groups that have other simple organic functional groups attached to them, for example, hydroxy, amino or nitro groups, or the chromophore can be attached directly to the α-carbon. For simplicity, all of the example structures will involve connection of the chromophore group to the α-carbon by way of a methylene (—$CH_2$—) group. Chromophore groups include but are not limited to fused aromatic systems such as pyrene, perylene, naphthalene, anthracene, phenanthrene and others of this type. We note that the point of attachment on the aromatic ring is variable. We also note that the synthesis of the individual amino acids containing these groups is analogous to that described for the pyrenylalanine in the specific example provided below. These syntheses are generally known to those skilled in the art.

TABLE 1

Naturally-Occurring Amino Acid Side Chains

Other chromophore functional groups that may be able to provide the same function include, but are not limited to, aromatic ketones such as benzophenone, acetylnaphthalene, acetylphenanthrene, and other functionalized fused aromatic molecules where the functional groups on the fused aromatic ring system may be alkyl, aryl, hydroxyl, halo, amino, nitro or others. The synthesis of amino acids containing these other groups will follow the same general procedure as outlined for the pyrenylalanine, although certain procedures may need to be employed to protect the functional groups during the synthesis and to deprotect them following synthesis. These synthetic procedures are known to those skilled in the art.

Figure 2:
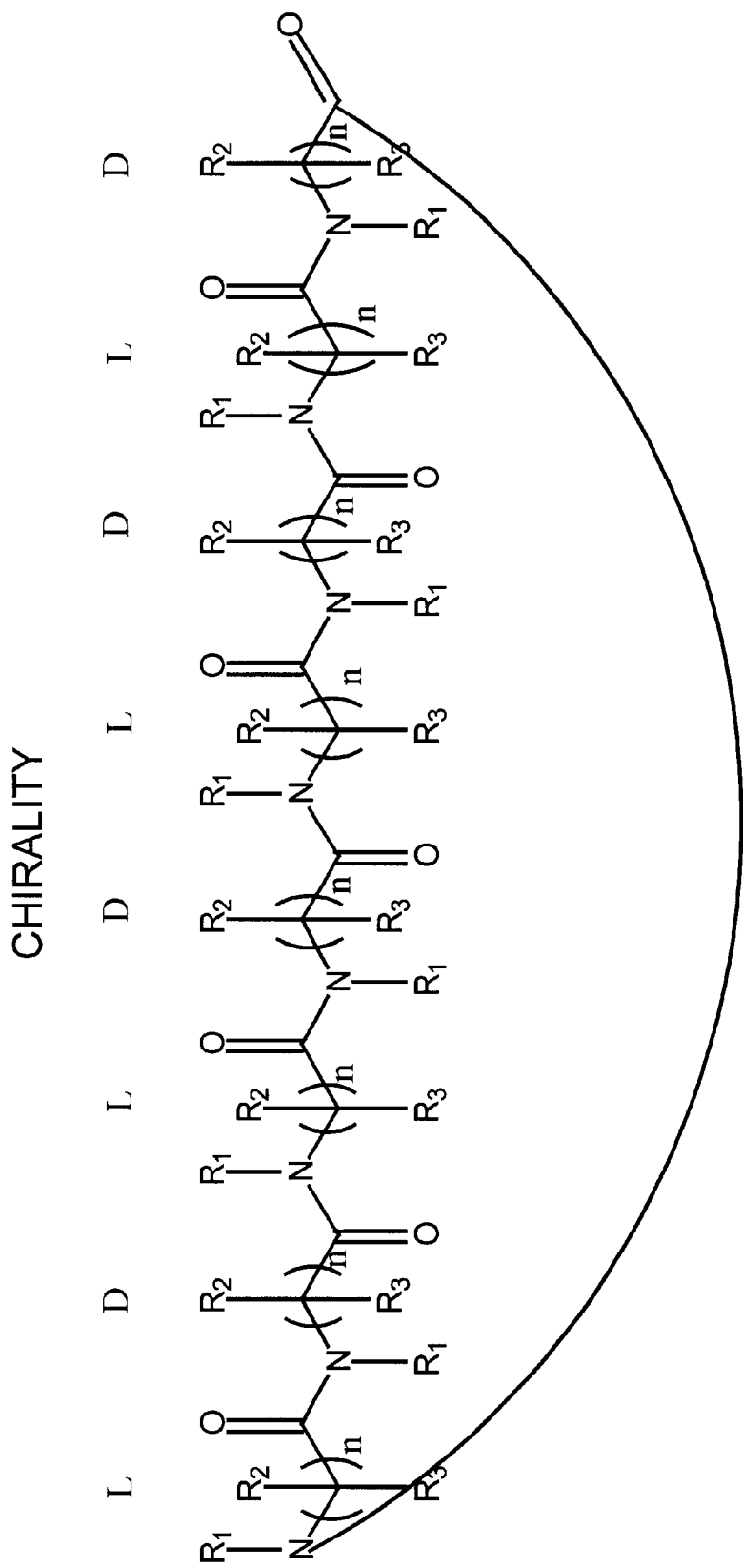
FIG. 2 shows a generalized 8-residue peptide structure of the present invention.

In FIG. 2, an example of a generalized structure for an 8-residue cyclic peptide is shown where the recurring unit of FIG. 1 is clearly evident. Here, again the amino acids may be either α or β (n=1 or 2). Eight-residue cyclic peptides containing all naturally occurring α-residues are known to stack into nanotubes. Here the $R_1$, $R_2$ and $R_3$ groups are as indicated above.

Figure 3:
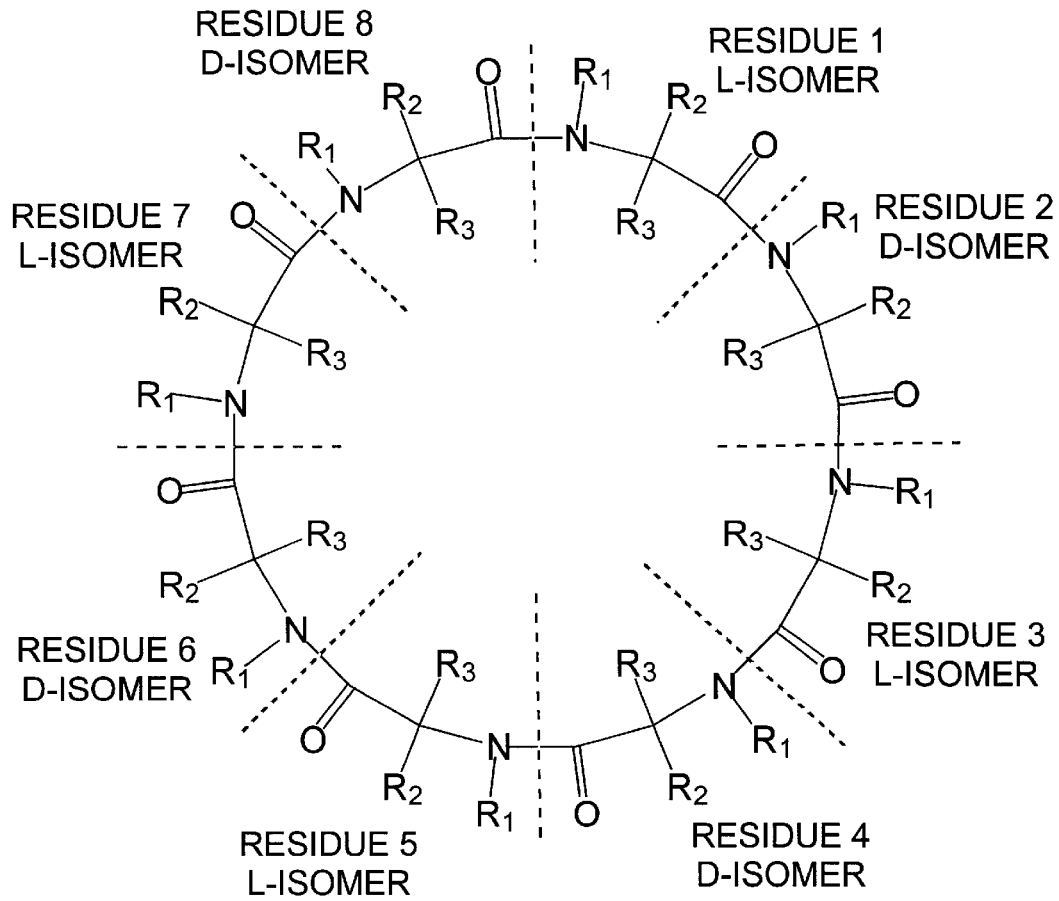
FIG. 3 shows a generalized 8-residue cyclic peptide structure of the present invention.

In FIG. 3, an example of a generalized structure for a cyclic, 8 residue octapeptide is shown in which all of the amino acid residues are α-amino acids. The $R_1$, $R_2$ and $R_3$ group designations are also as described above.

Figure 4:
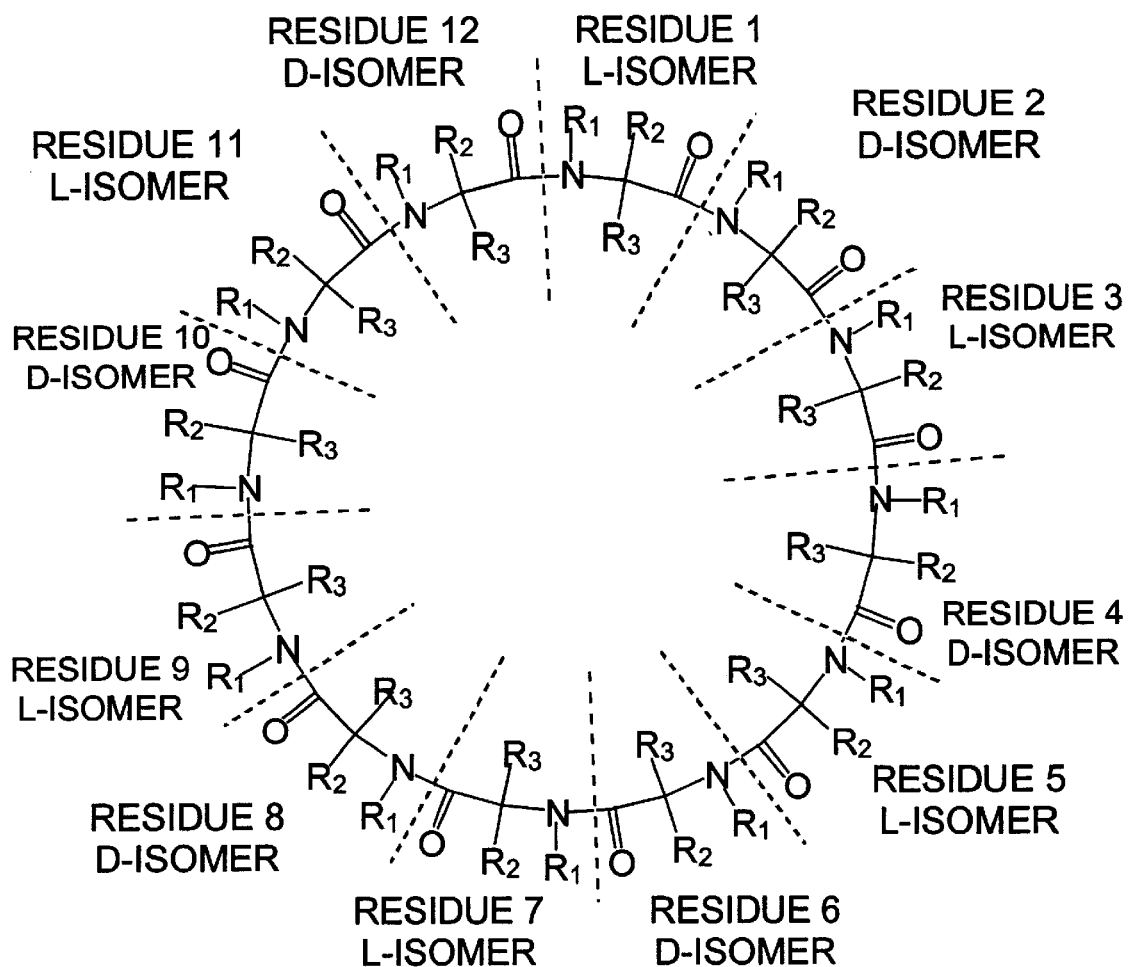
FIG. 4 shows a generalized 12-residue cyclic peptide structure of the present invention.

In FIG. 4, an example of a generalized structure for a cyclic, 12 residue dodecapeptide is shown in which all of the residues are α-amino acids. The $R_1$, $R_2$ and $R_3$ groups are again the same as above.

Figure 5:
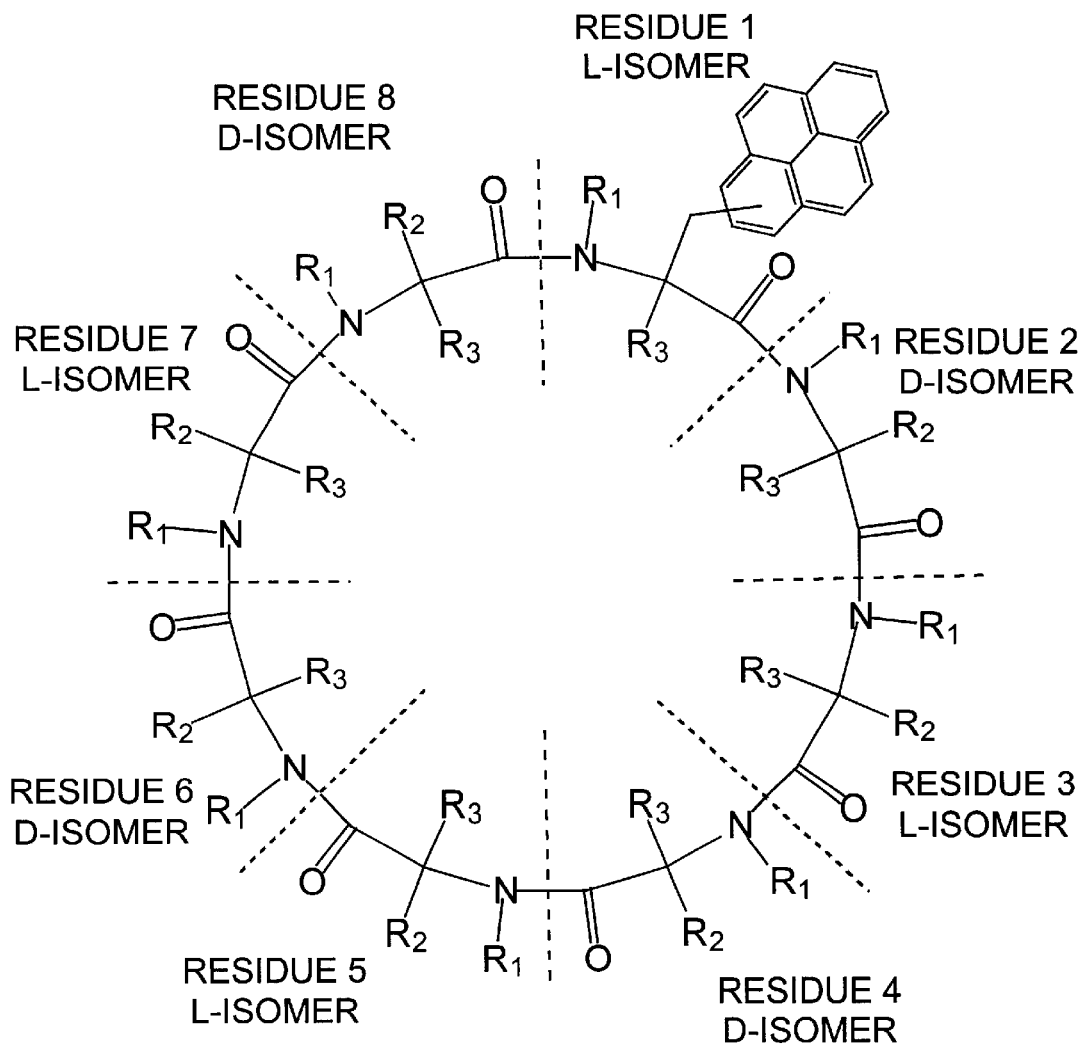
FIG. 5 shows a generalized 8-residue cyclic peptide structure comprising a pyrene chromophore.
Figure 6:
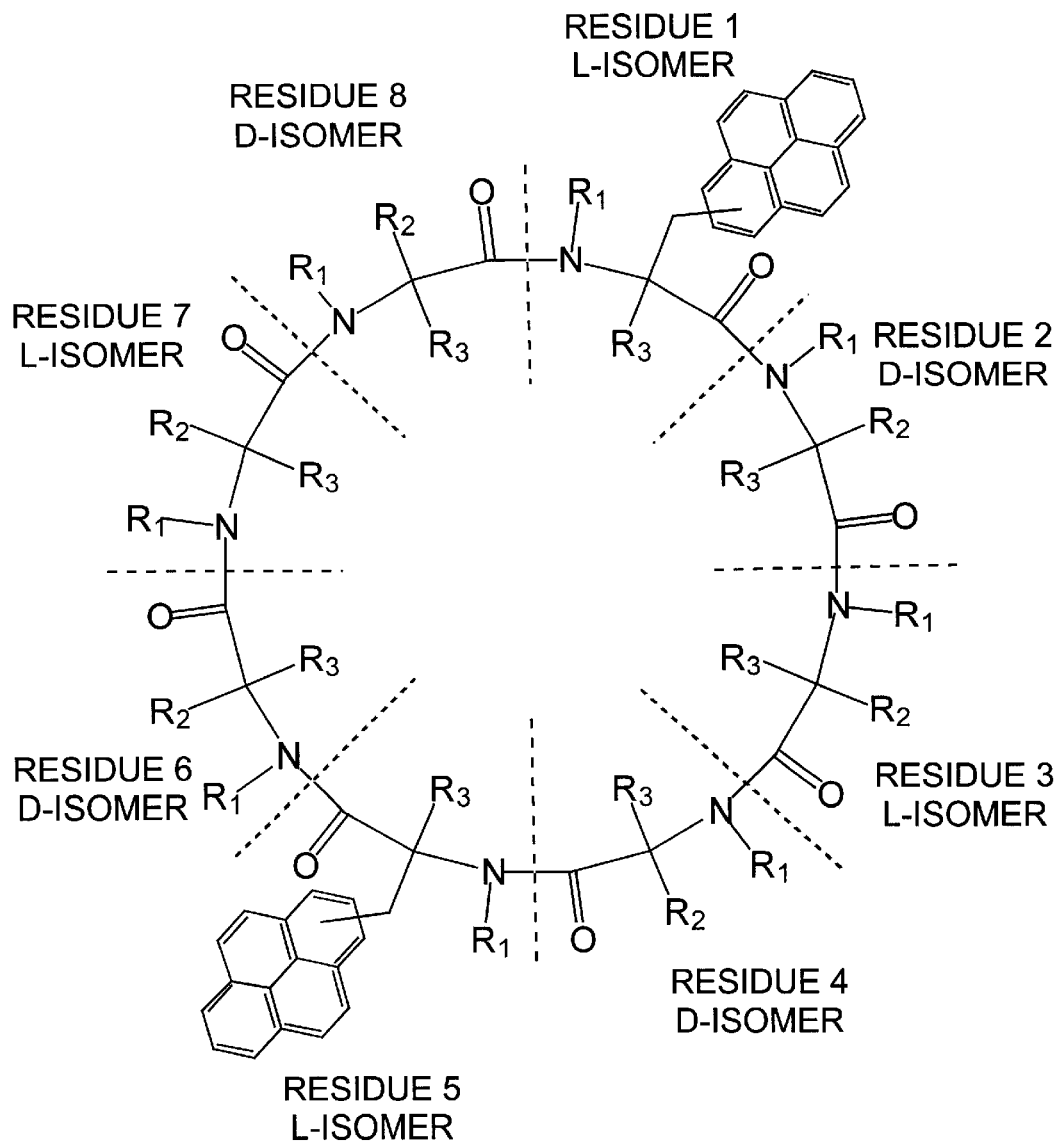
FIG. 6 shows a generalized 8-residue di-pyreneyl cyclic peptide structure of the present invention.
Figure 7:
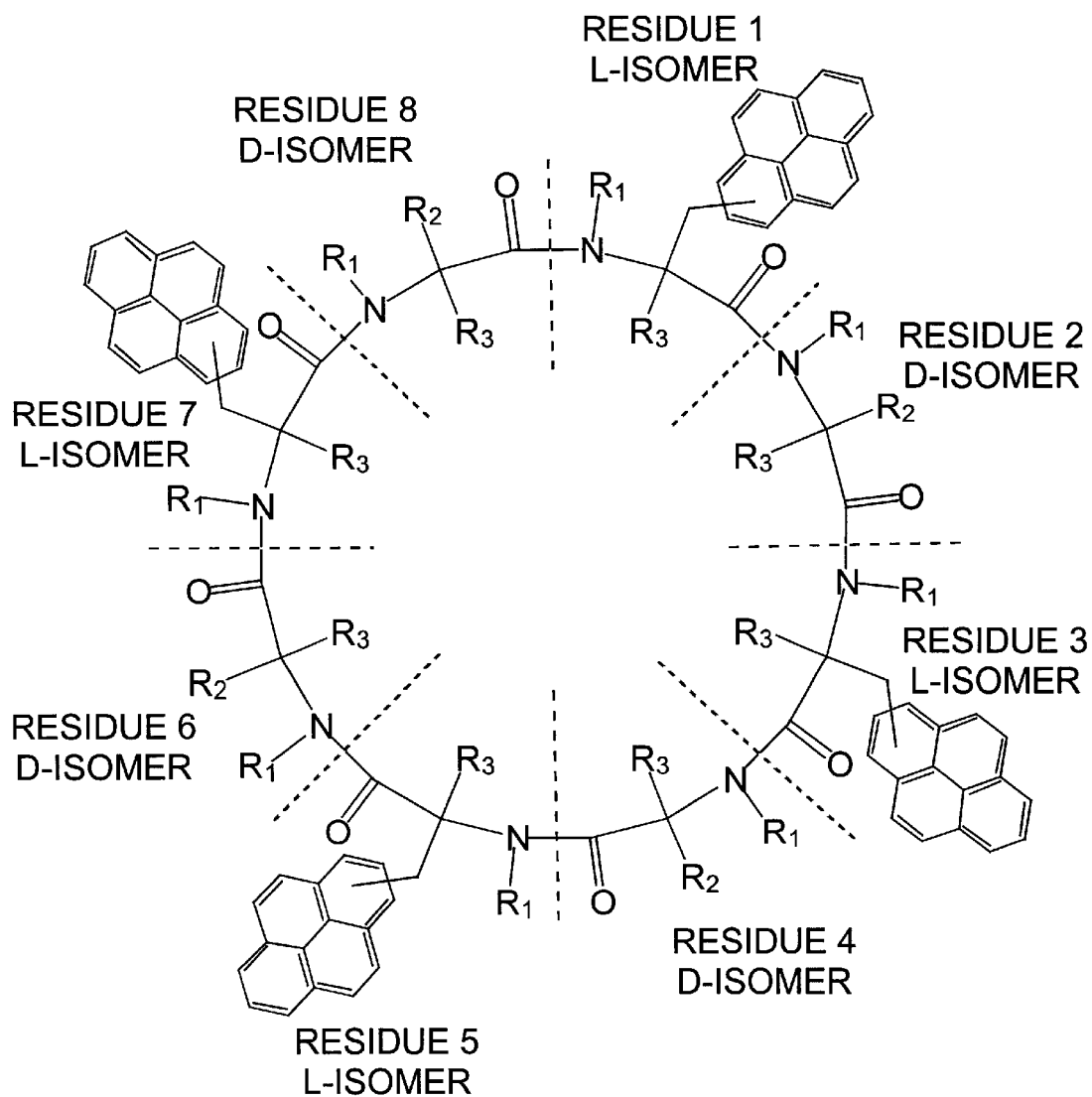
FIG. 7 shows a generalized 8-residue tetra-pyreneyl cyclic peptide structure of the present invention.
Figure 8:
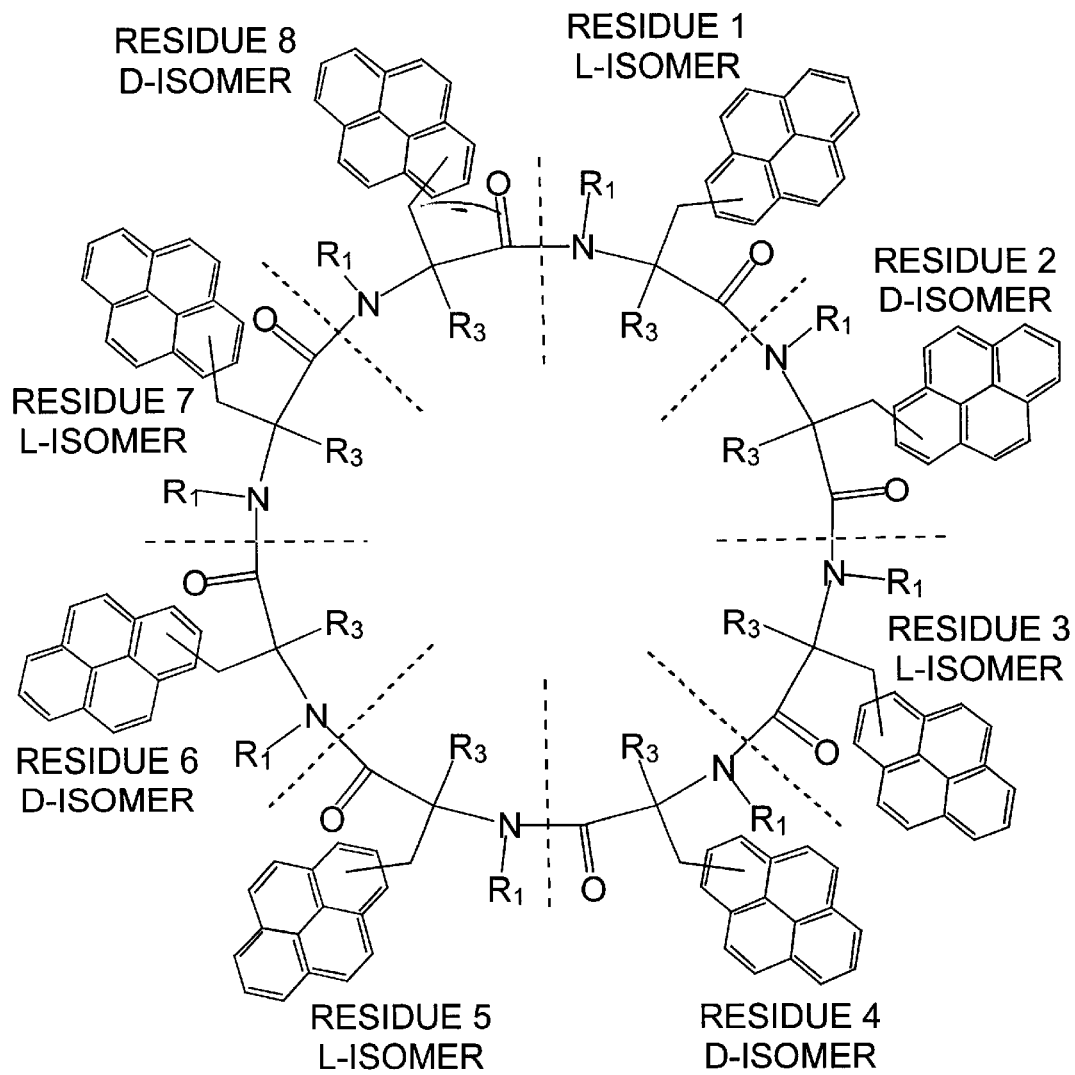
FIG. 8 shows a generalized 8-residue octa-pyreneyl cyclic peptide structure of the present invention.
Figure 9:
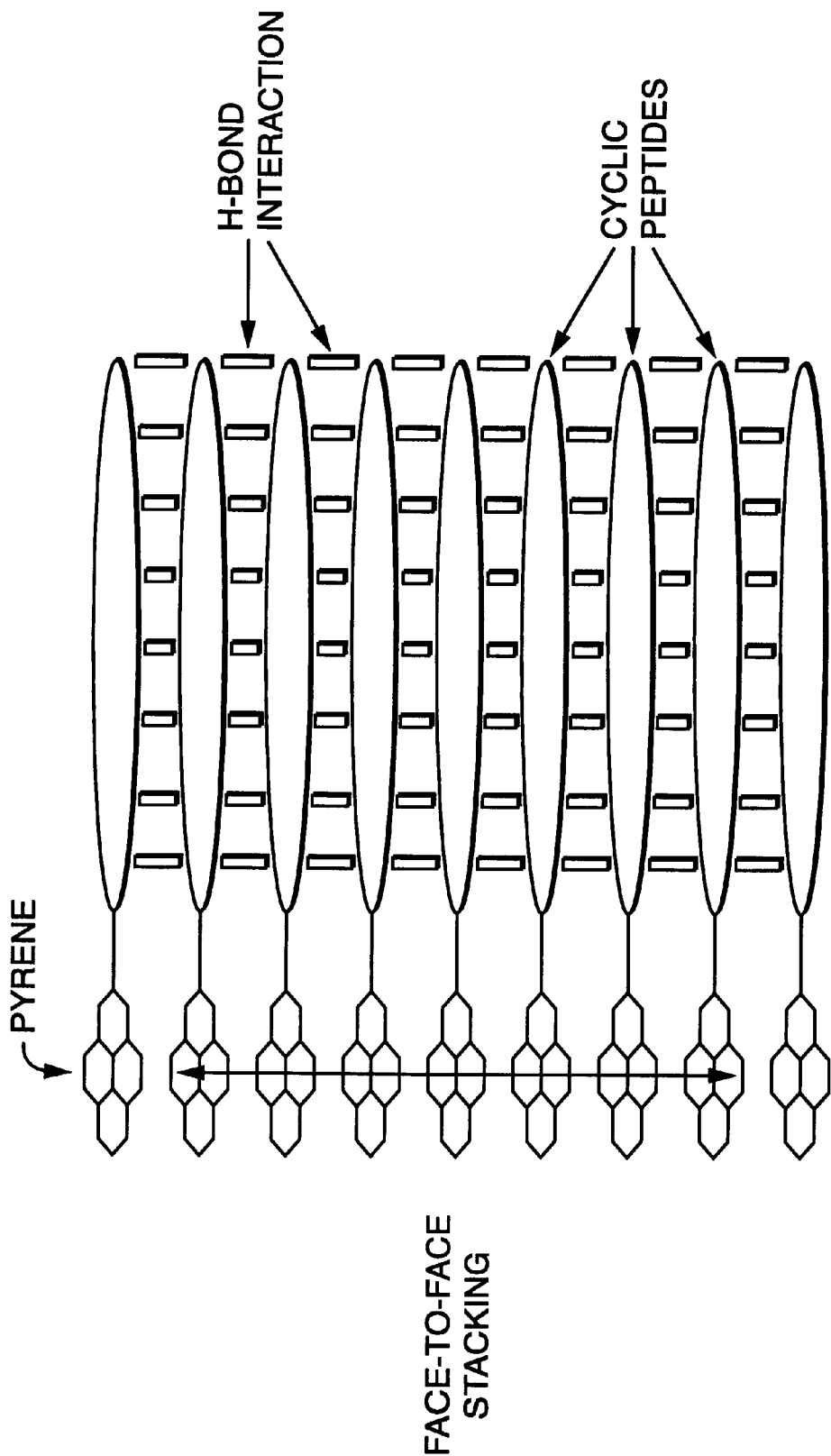
FIG. 9 shows a schematic of a seven-layer cyclic peptide nanotube with face-to-face stacking of the pyrene chromophores.

FIG. 5 shows an example of a generalized cyclic octapeptide structure in which all but Residue 1 are alanine amino acids. Residue 1 is a chromophore containing amino acid, pyrenylalanine. The point of attachment of the pyrene is variable. In FIG. 5, the linking group between the peptide backbone and the pyrene is a methylene (—$CH_2$—) group. This cyclic peptide with one pyrene group is the simplest pyrene-containing cyclic peptide monomer capable of forming a nanotube and exhibiting conductive behavior. Other cyclic peptides having increasing numbers of pyrene residues will exhibit higher conductive behavior. For example, FIG. 6 shows a generalized cyclic alanine octapeptide structure containing two pyrene groups at residue positions 1 and 5. It is worth noting that the choice of residue position at which the numbering begins is arbitrary. In FIG. 7, a generalized cyclic octapeptide structure containing four pyrene residues at positions 1, 3, 5 and 7 is shown and, in FIG. 8, a generalized structure with eight pyrenes is shown. By way of example, it is anticipated that, for cyclic octapeptide structures, 1 to 8 pyrenylalanine residues may be successfully employed. For larger 12 residue structures, up to eight chromophore residues may be employed. FIG. 9 and FIG. 10 provide a schematic representation of a stacked array of di-pyrenyl cyclic peptide where the cyclic peptides form a nanotube structure through hydrogen bonding and the pyrene residues stack face-to-face to provide maximum π orbital overlap for enhanced conduction. It is important to note that, for simplicity, these figures show a only a small portion of a nanotube structure which may comprise more than 2000 cyclic peptide layers.

Whether there are preferred residue positions for the chromophores will depend on the number of chromophore groups that are incorporated into each cyclic peptide monomer, the total number of amino acid residues in the cyclic peptide, and the chirality of the residues containing the chromophores. Cyclic peptides have been shown to stack into peptide nanotubes in an anti-parallel fashion in which L-isomers in one cyclic peptide lie on top of L-isomers in another cyclic peptide. This also applies to D-isomers. For discussion purposes, we use as an example a cyclic octapeptide containing all α-amino acids. Optimum face-to-face π—π overlap of the chromophores can be achieved with 2 or more chromophore-containing residues in the peptide as long as the chirality of these residues is the same. In fact with three or more residues containing chromophores with the same chirality, π—π overlap of the chromophores throughout the nanotube is guaranteed. In cyclic octapeptides containing up to 4 chromophores, π—π overlap will be optimized if all four of the chromophore-containing residues have the same chirality. In general, the greater the number of chromophore-containing residues, the greater the efficiency of the invention. However, we expect that cyclic octapeptides, for example, will have device function for cyclic peptides containing 1 to 8 chromophores. It is important to note that the stackable cyclic peptides of the present invention have alternating chirality. Therefore the preferred positions of the chromophore-containing residues are determined by their chirality.

Figure 18:
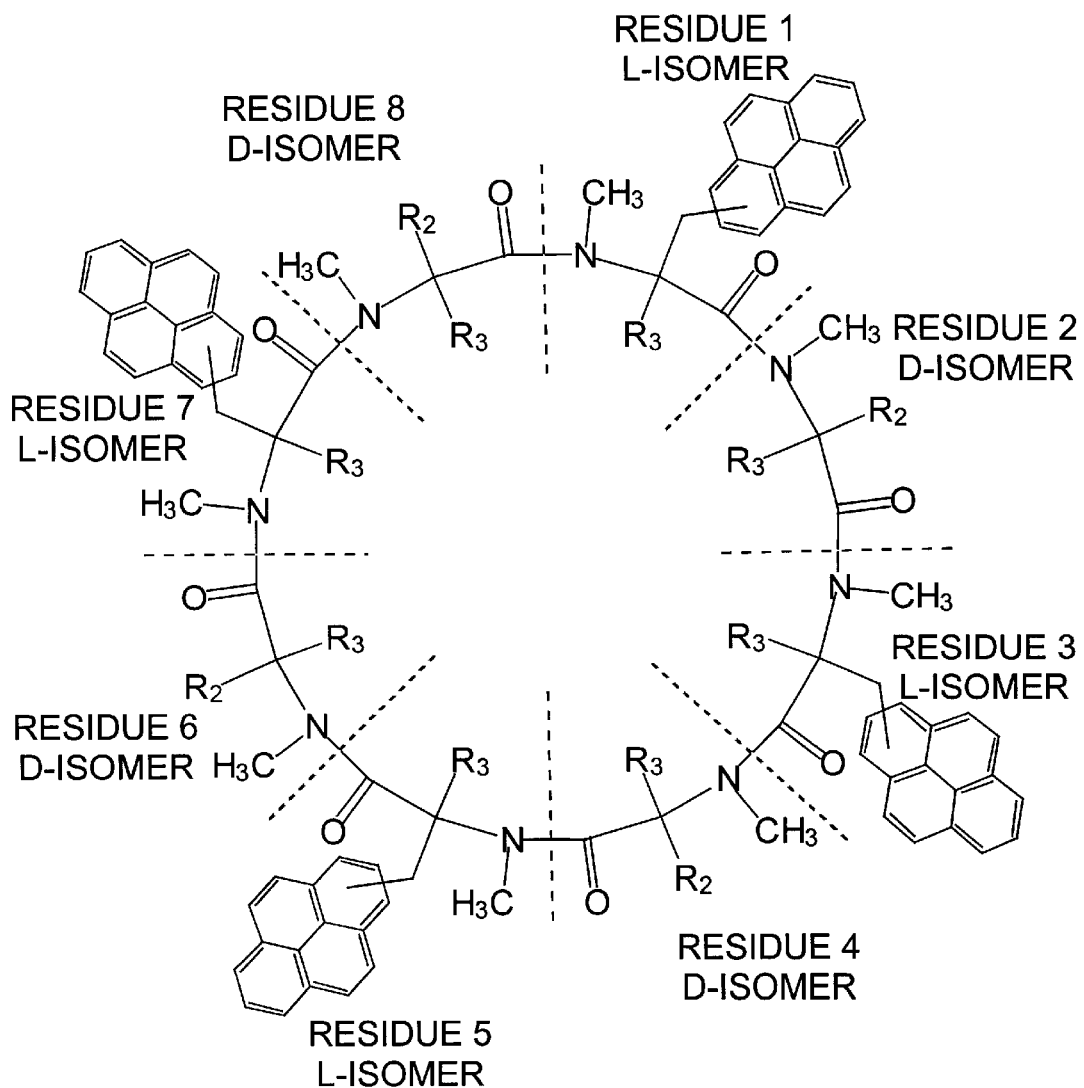
FIG. 18 shows one embodiment of a tetra-pyreneyl cyclic peptide employed for terminating a nanotube of the present invention.
Figure 19:
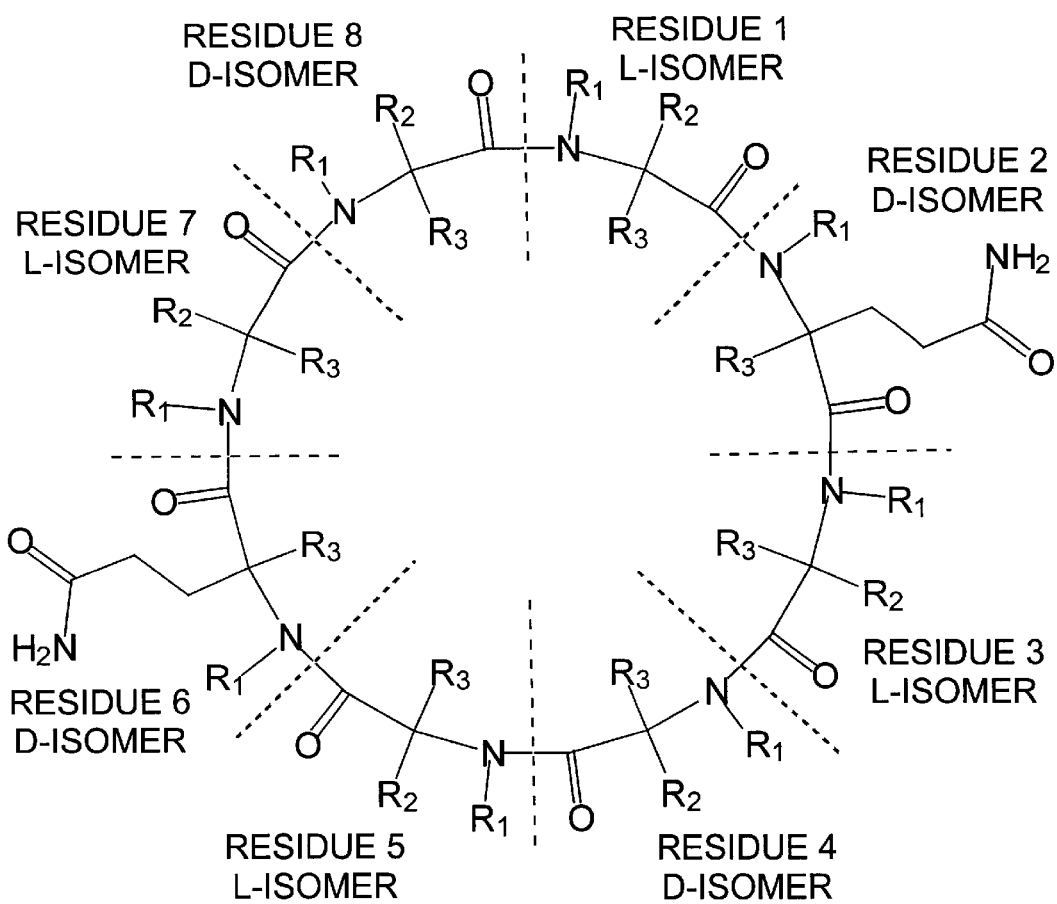
FIG. 19 shows one embodiment of an 8-residue cyclic peptide with glutamine side chains for side-to-side hydrogen bonding of cyclic peptide nanotubes.

A number of alternative cyclic peptide structures have specific roles in forming cyclic peptide nanotubes. For example, it may be desirable to control nanotube length by capping the end on the cyclic peptide stack with a non-stacking cyclic peptide. FIG. 18 shows an example of a generalized tetra-pyreneyl, cyclic octapeptide structure that may be used to cap a growing nanotube. With this structure, the nitrogen methyl groups prevent continued nanotube growth by restricting hydrogen bonding to only one side of the molecule and preventing stacking of a subsequent cyclic peptide layer. FIG. 19 shows another useful cyclic peptide structure where the glutamine side chains promote side-to-side hydrogen bonding of nanotubes to form thin films made from a plurality of nanotubes. Other residues may be employed as well, such as uncharged and charge polar amino acid and chromophore side chains and other hydrogen bond donors or acceptors.

All of the structures proposed above may be employed with a variety of chromophores. For non-linear optical materials, chromophores are selected to provide electron donor and electron accepting properties in the same cyclic peptide monomer. In these applications, it is preferable that the donor and acceptor chromophore residues be placed adjacent to one another for optimum performance. In a preferred embodiment, the donor and acceptor residues are positioned with a spacing of 3.5 to 4.0 angstroms for optimum performance. Examples of electron donors include but are not limited to aliphatic and aromatic primary, secondary and tertiary amines, hydroxybenzenes, for example single or multiple hydroxy groups such as anisole or veratrole, and other hydroxyaromatics or aromatic hydrocarbons. Examples of electron acceptors include but are not limited to aromatic hydrocarbons, aromatic hydrocarbons that contain cyano, nitro, carboxyl, etc, ketones, aromatic ketones, quinones and other ketone structures. The synthesis of enantiomerically pure amino acids containing these groups will follow the generalized synthetic procedures and methods disclosed herein and are generally known to those skilled in the art.

In one embodiment of the instant invention shown in FIGS. 7 and 9, cyclic peptides are fabricated from a series of eight alanine residues. Fabricated structures are not limited to eight residues. To obtain the flat, disk-like conformation of the cyclic peptide that is necessary for stacking, the amino acids in the chain alternate between the D- and L-optical forms. The embodiment shown in FIG. 7 consists of unsubstituted alanine residues that alternate with residues synthesized to contain pyrene functional groups. Pyrene is a large planar aromatic molecule that is known under some conditions to form face-to-face dimers and exciplexes which exhibit charge and energy transfer behavior. Self-assembly of the cyclic peptides into nanotubes results in spatial overlap of the wave functions of pyrene groups on adjoining cyclic peptides, thereby facilitating electronic communication between the pyrene groups resulting in energy and/or charge transfer. FIG. 9 is a schematic representation of a nanotube formed from stacked layers of the cyclic peptide shown in FIG. 7. In the example shown in FIG. 9, only one pyrene group per cyclic peptide layer is shown for simplification.

Since one potential application of the chromophore-substituted cyclic peptide nanotubes is as a molecular electronic wire or switch, another embodiment of the present invention is designed to facilitate linking of the cyclic peptide nanotube with conventional electronic circuitry. This is achieved by incorporating cysteine residues into the cyclic peptide structure in place of one or more of the alanine residues that do not contain pyrene chromophores. For example, in one embodiment four alternating cysteine residues may be incorporated into a cyclic peptide structure. In other embodiments, other numbers and positions of these residues may be used.

There is ample precedent in the literature for the formation of covalent bonds between cysteine residues and gold surfaces such as are used in electronic circuitry. The thiol functionality of cysteine provides the site of attachment in that sulfur-gold bond formation takes place. Thus, in the example embodiment shown in FIG. 20, the cyclic peptide nanotube that incorporates pyrene-substituted alanine residues and cysteine residues provides for both electronic conduction capabilities within the peptide structure, via the pyrene groups, and conduction between the nanotubes and conducting gold substrate surfaces.

A number of characterization methods are useful for confirming the structures of cyclic peptide molecules. These include Mass Spectral Data as well as UV-Visible absorption and Fluorescence emission spectra. They confirm the synthesis of individual monomeric cyclic peptide molecules consisting of eight amino acids and containing a variety of chromophores, including pyrene, benzophenone and naphthalene, all of which provide potential molecular electronic and photonic functionality to the supramolecular systems that are formed by self-assembly of the monomeric units. The data also confirms that the monomeric units stack such that in the case of the pyrene-containing peptides, the pyrene chromophores are also stacked in a face-to-face geometry that facilitates electronic communication between the pyrene groups. Characterization of the primary and secondary structures of the instant invention may be performed by well-known procedures including NMR and circular dichroism. Optical spectroscopic techniques such as steady state and time-resolved fluorescence and phosphorescence and transient absorption permit characterization of the charge and energy transfer characteristics of the nanotubes.

The devices of the present invention may employ a wide range of amino acid sequences and a wide range of chromophores to provide desired functionality for conductivity or non-linear optical behavior. Peptide sequences that form cyclic peptide stacked nanotubes can be synthesized from nearly all of the 20 naturally occurring amino acids in addition to a wide range of unnatural and chromophore-containing amino acids. It is anticipated that a diverse range of device functionality may be achieved using a variety of poly fused aromatic, donor-acceptor and other chromophores. Examples of such chromophores include but are not limited to the following parent chromophores: pyrene, benzophenone, naphthalene, phenanthrene, anthracene, fluorene, carbazole, polyaromatics in general, fused aromatics in general, porphyrins and porphyrin analogs, both metal-containing and metal-free, and aromatic ketones other than benzophenone. It is important to note that for each compound listed above, device functionality may also be achieved with single or multiple substitution of the parent chromophore molecule with other functional groups.

Specific applications of these types of cyclic peptide chromophore systems include but are not limited to:

a. Pyrene containing peptide nanotubes which can provide a conduit for the flow of charge over large distances, for example, as a molecular scale wire. These structures can also be modified with thiol groups such that they can be caused to self-assemble onto conducting surfaces such as gold, thereby providing a means of communication between the molecule and the macroscopic world. The end-uses of this system include but are not limited to nanocircuitry in computing applications and nanoscale memory devices.

b. The attachment of chromophores other than pyrene to nanotubular peptides enables other potential applications over and above the electrical conduction and storage applications anticipated for the pyrene-containing units. For example the incorporation of electron donating and electron accepting chromophores in a single cyclic peptide monomeric unit may result in a self-assembled nanotube in which the donor/acceptor chromophores of separate monomeric units interact strongly. This interaction is expected to result in strong non-linear optical phenomena as has been observed in other, non-peptide, donor/acceptor systems. This strong interaction may also be useful for directing the self-assembly process itself. In other words, the donor/acceptor interaction may help the cyclic peptides to stack in a single particular arrangement.

c. By appropriate selection of individual residues of the peptide, it is possible to prevent stacking thereby leaving the monomeric cyclic peptides unassociated with other monomers. Under these circumstances, it is possible to create device operation from the single monomeric units themselves. For example, the inclusion of three chromophores, A, B and C, with different oxidation potentials may allow the production of a transient molecular scale magnet. The individual chromophores A, B and C would be chosen such that the oxidation potentials of each chromophore would decrease in a clockwise fashion as one proceeds around the cyclic peptide starting with A as the highest oxidation potential and ending with C as the lowest oxidation potential. In one embodiment, a charge would be introduced onto one of the chromophores A, either electrochemically or by photoexcitation followed by ionization. A series of oxidation steps would follow resulting ,in the flow of the positive charge around the cyclic peptide in a clockwise fashion. This charge flow is expected to provide a transient magnetic field on a molecular scale just as charge flowing through a circular copper coil produces a magnetic field on a macroscopic level. When the positive charge has reached chromophore C it remains localized at this spot because the next chromophore in the peptide is A and the previous chromophore is B, each of which have higher oxidation potentials than C and therefore cannot be oxidized by the positively charged C. However, photoexcitation of C+ can produce an excited state with a higher oxidation potential of either A. This will result in oxidation of A and therefore the regeneration of A+, thereby starting a new cycle. If the source used for the photoexcitation of C+ is continuous, a molecular scale magnetic field can potentially be maintained continuously. We have previously published work that shows positive charges can be moved from one chromophore to the next within a single molecule by photoexcitation.

Synthesis of Chromophores

Figure 12:
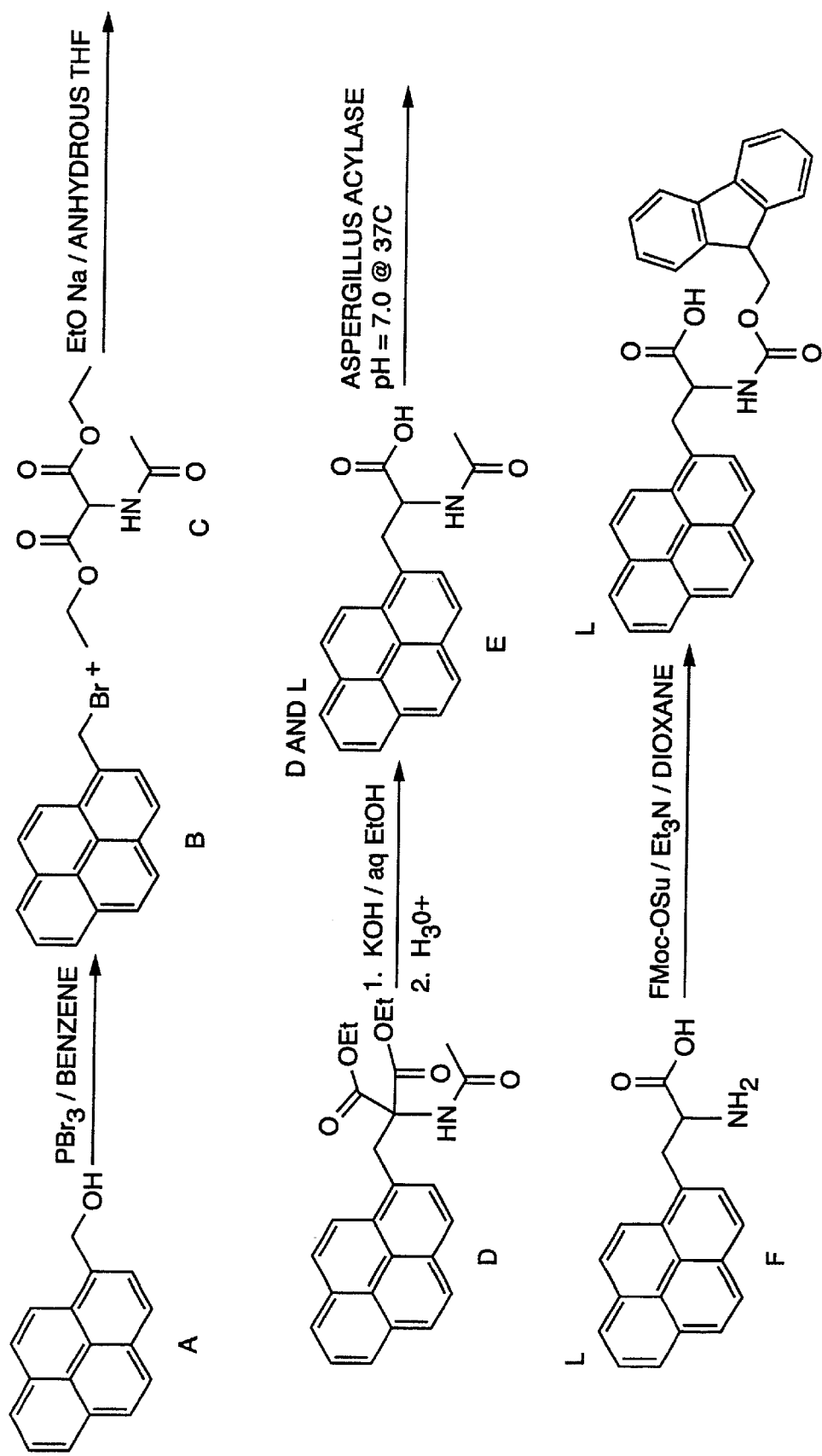
FIG. 12 is an example synthesis method for a N- Fmoc-L-pyrenyl alanine (Fmoc-pya) chromophore employed in the present invention.

The synthesis of chromophore-containing amino acids generally follows that outlined for the specific example of N-Fmoc-L-pyrenyl analine (Fmoc-pya) shown in FIG. 12. This method generally involves the conversion of the chromophore-substituted methanol (labeled A) to a halomethyl aromatic (B). B is added to diethylacetamidomalonate (C) in the presence of base to yield the adduct (D). Removal of an ester group with base followed by acidification yields a racemic mixture of the N-acylated amino acid (E). Since pure optical isomer is used in the syntheses of cyclic peptides, the racemic mixture is enzymatically-resolved using Aspergillus Acylase which selectively deacylates the L-isomer, yielding pure separated L- and D-isomers (F). In the peptide synthesis, it is necessary to protect the N-terminus of the amino acid and for this reason, the Fmoc (fluorenylmethoxycarbonyl) group is attached to give the final protected Fmoc-L-pyrenyl alanine.

Figure 11:
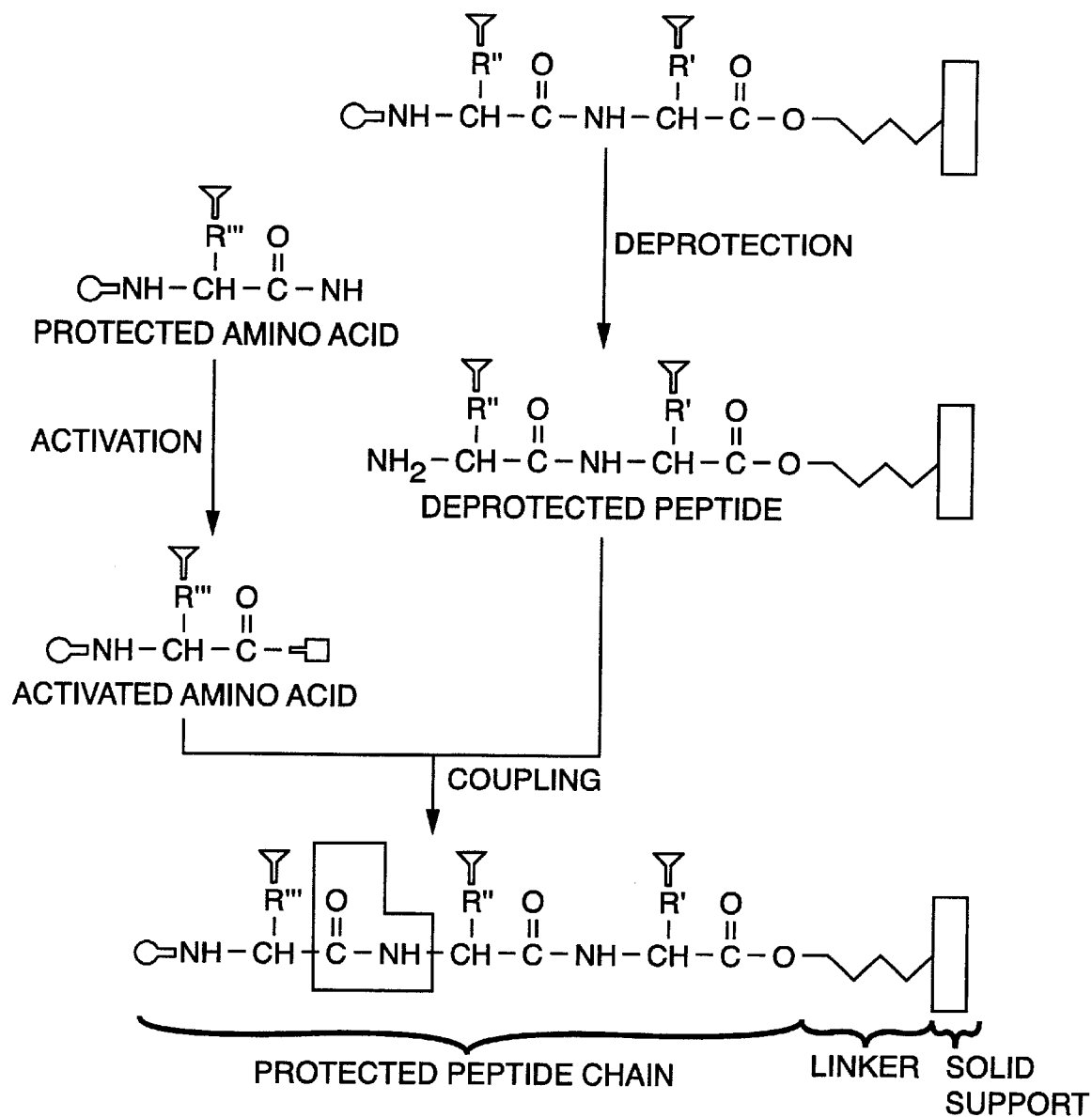
FIG. 11 is a schematic of the solid-phase cyclic peptide synthesis method employed with the present invention.

Peptide synthesis generally adheres to the method shown schematically in FIG. 11. We have used a variety of polymer resins as solid phase supports. For example, a Wang resin is well suited to the Fmoc protection strategy. The resin is obtained either pre-loaded with an amino acid or is loaded with an amino acid by standard methods known in the art. There follows a series of steps that include: a) removal of the Fmoc protecting group of the amino acid that is attached to the resin using base, for example piperidine; b) addition of the next amino acid to be attached to the peptide; c) activation of the carboxylic acid group of this amino acid with standard activating agents, for example HOBT, Pybop or other agents; and d) removal of unreacted components. These steps are repeated for each amino acid added to the peptide. When the last amino acid is added, the peptide is cleaved off the resin with acid, for example trifluoroacetic acid, to yield a peptide that has a free acid function at one end and an Fmoc protected amine at the other. In order to cyclize the peptide, the carboxylic acid is converted to a more reactive acid chloride using sulfonyl chloride or oxalyl chloride, the amine is deprotected and the acid chloride and amine are allowed to couple. This yields the cyclic peptide.

By way of example, for the synthesis of N-Fmoc-L-pyrenyl alanine (Fmoc-pya), the first Fmoc amino acid is initially attached to an insoluble support resin via an acid labile linker. Deprotection of the Fmoc, is accomplished by treatment of the resin with a base, usually piperidine. The second Fmoc amino acid is coupled utilizing a preactivated species or in situ activation. After the desired peptide is synthesized, the resin bound peptide is deprotected and detached from the solid support via TFA cleavage.

Figure 13:
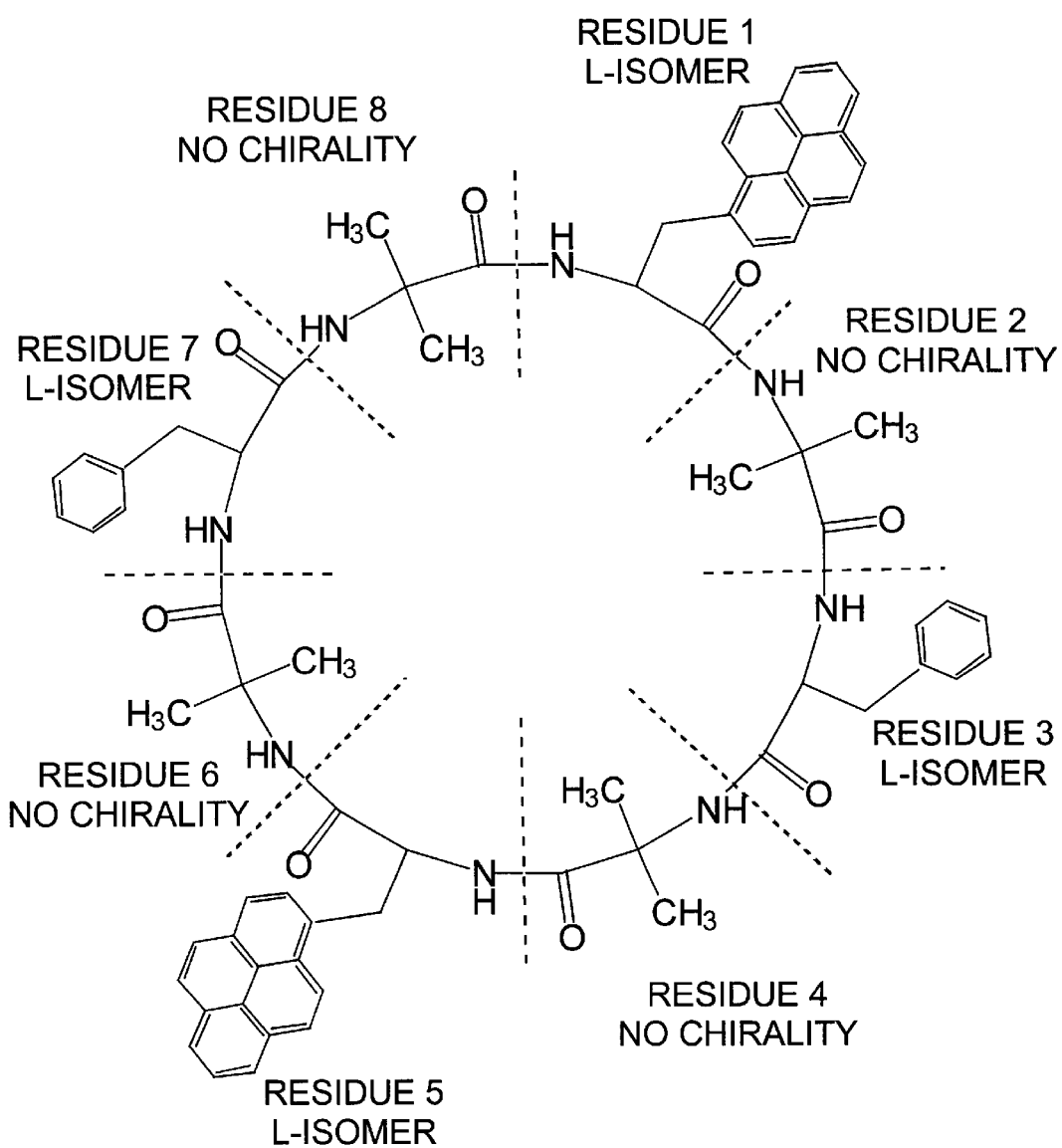
FIG. 13 shows a non-stacking di-pyreneyl cyclic peptide structure.
Figure 14:
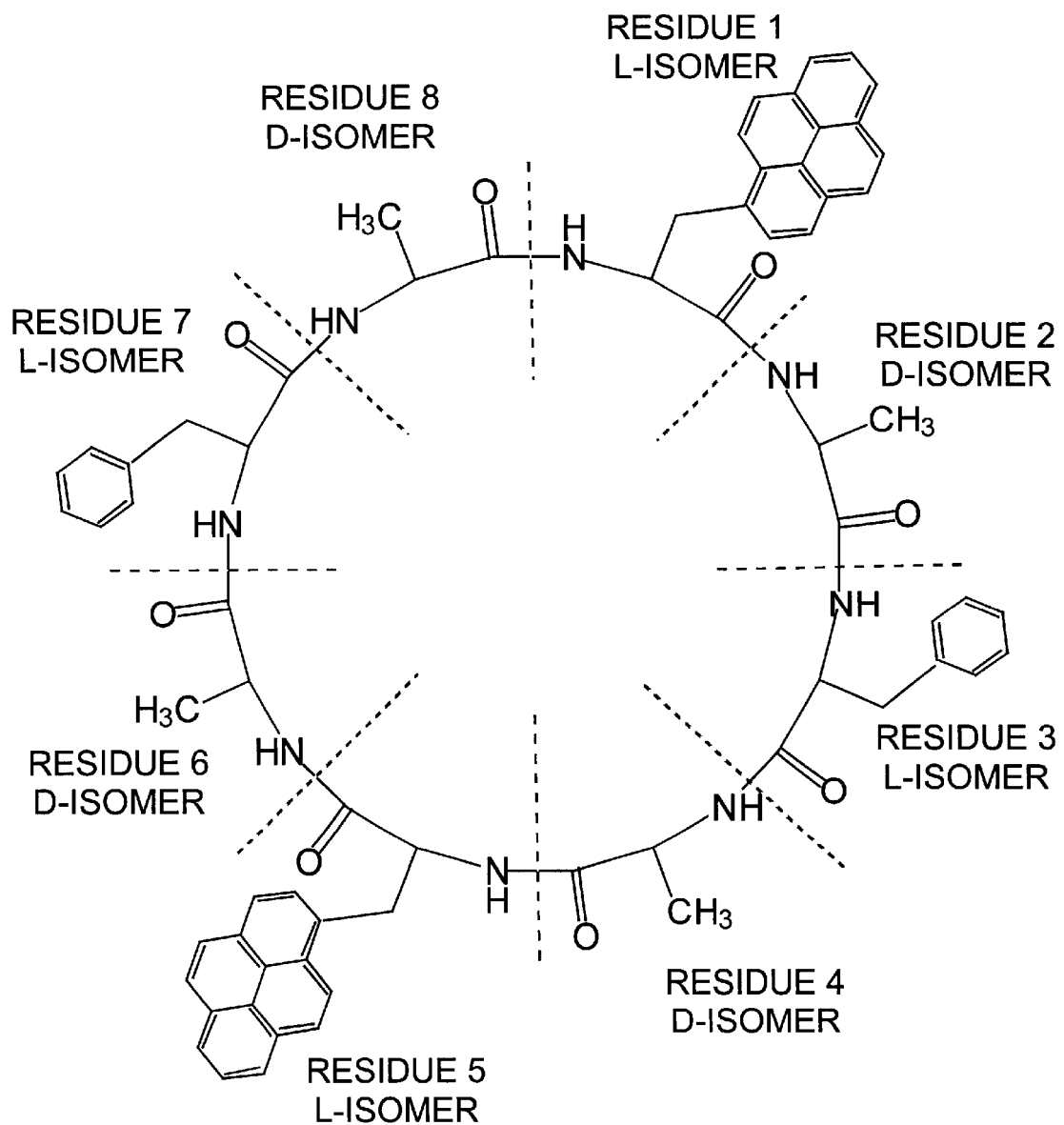
FIG. 14 shows a stacking di-pyreneyl cyclic peptide structure.
Figure 15:
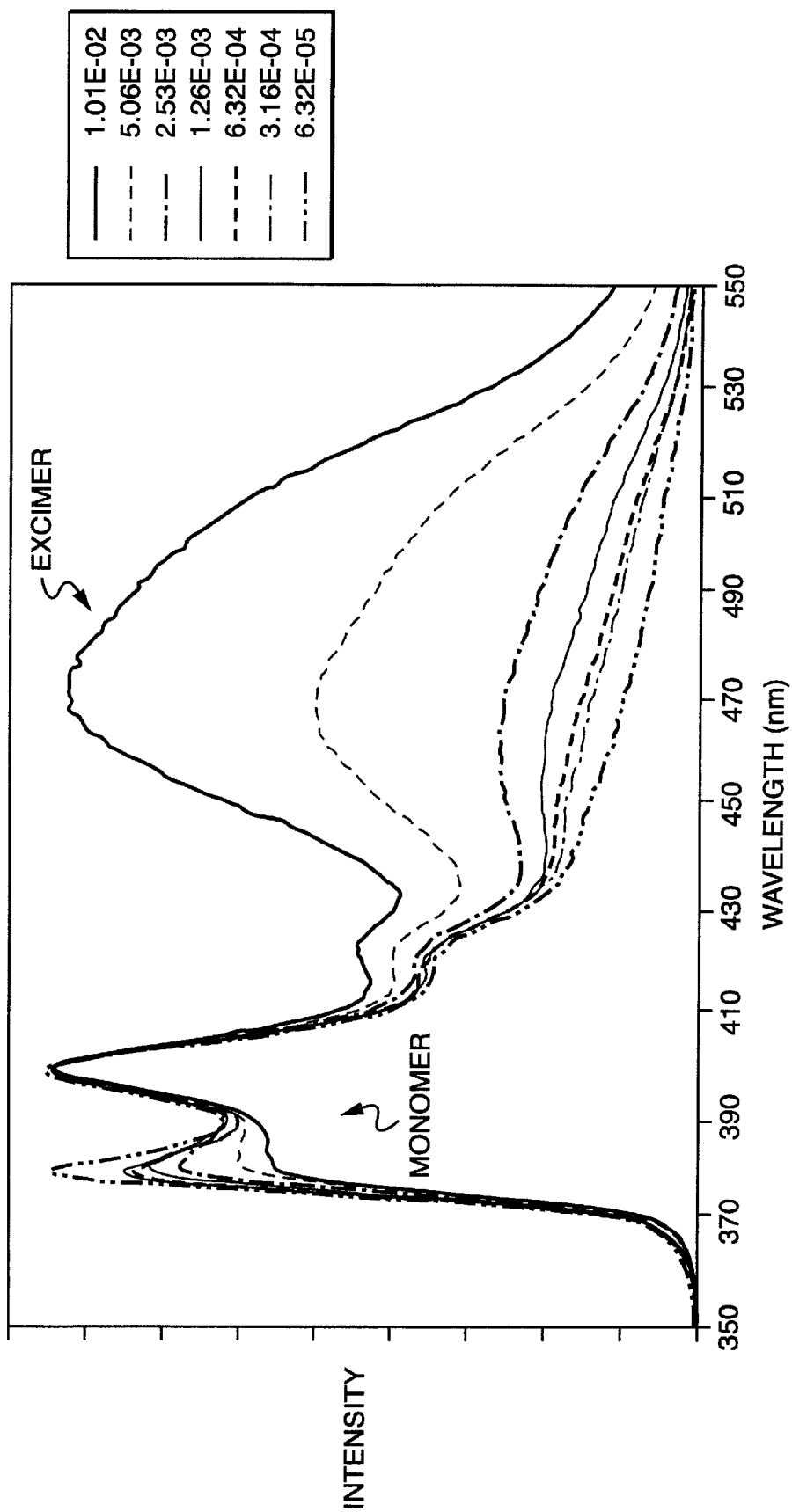
FIG. 15 shows the concentration dependence of excimer fluorescence for the non-stacking cyclic peptide shown in FIG. 13.
Figure 16:
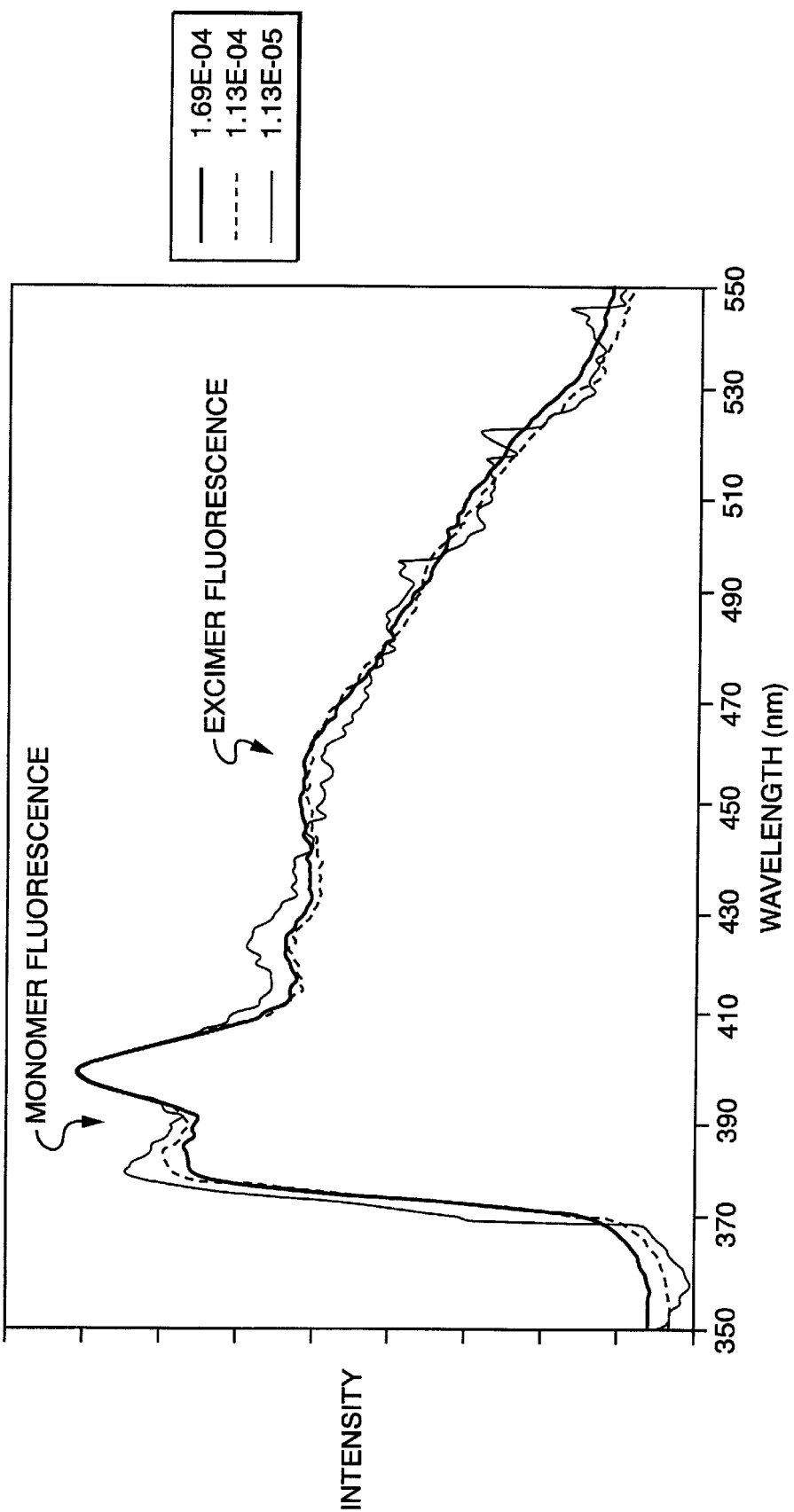
FIG. 16 shows the absence of concentration dependence of excimer fluorescence for the stacking cyclic peptide shown in FIG. 14

By way of example, we have chosen two cyclic peptides to demonstrate this idea. The example cyclic peptide shown in FIG. 14 contains of two pyrenyl alanine residues interspersed with alanine and phenylalanine residues. Cyclic peptides containing alanine are known to stack into nanotubes. The other peptide shown in FIG. 13, contains aminoisobutyric acid in place of alanine. Because of steric interactions, these cyclic peptides do not stack. The presence of pyrene in the peptides is important for two reasons. First it is the pyrenes that will provide electronic conduction in nanotubes through face-to-face interactions when the peptides stack. Second the pyrenes are a probe for the demonstration of the stacking process itself. When pyrene is photoexcited, it emits light in the 400 rim region of the spectrum. This is called monomer fluorescence because it originates from individual pyrene molecules. However, when two or more pyrenes form face-to-face complexes in the excited state (excimers) they emit light that is red-shifted to 460 rim. Thus, we expect to observe monomer-type fluorescence in our non-stacking peptide (see FIG. 15), but excimer-type fluorescence in our stacking peptide (see FIG. 16). In fact, in both peptides, we observe both kinds of fluorescence but there is an important distinction. As shown in FIG. 15, the non-stacking peptides exhibit excimer fluorescence only at very high concentrations and the intensity of excimer fluorescence is dependent on concentration. This is behavior that is observed in pyrene itself and is due to intermolecular interactions, that is two pyrenes in separate peptides are interacting. As shown with FIG. 16 with the stacking peptide, excimer fluorescence is observed at much lower concentrations and its intensity is independent of concentration as would be expected from an 'intra-stack' interaction.

Synthesis of N-BOC-An-Ala

1. Synthesis of Diethyl-(9-anthryl methyl)-[N-(tert-butoxycarbonyl)amino) Malonate 1.7 g of diethyl 2-[N-(tert-butoxycarbonyl)amino] malonate was added to a 10 gm of ice anhydrous DMF solution involving 1.2 eq of sodium hydride and 0.5 eq of lithium bromide, stirring for 1 hr under nitrogen and ice-bath. 0.5 eq of anhydrous ethanol was dropped slowly during 1 hr of ice-bath. 1.2 g of 9-chloromnethylanthracene in 10 ml of anhydrous DMF was added slowly, heated at 80° C. for 18 hours. Removing the solvent on a rotary evaporator. Distilled water was added and the product was extracted with ethyl acetate, and washed by 5% citric acid. The solvent was removed by rotary evaporator. The crude product was recrystallized in ethanol. 1.3 g of yellow solid was obtained. The yield was about 53%. [$^1$H-NMR(chloroform-d) $\delta$1.24 (t, 6H, 2×CH$_3$), $\delta$1.49 (s, 9H, CH$_3$), $\delta$3.98, 4.15 (m, 4H 2×CH$_2$), $\delta$4.73 (s, 2H, CH$_2$), $\delta$5.47 (s, 1, NH). $\delta$7.45 (4H, Ar-2, 3, 6, 7), 8.01 (2H, 4, 8), 8.30 (2H, Ar-1, 5), 8.40 (s, 1H, Ar-10)]

2. Synthesis of (D,L) 9-Anthryl Alanine 1.3 g of diethyl (9-anthryl methyl)-[N-(tert-butoxycarbonyl) amino] malonate was mixed with 4 eq of sodium hydroxide in 10% water-ethanol solution, refluxing for four hours. Ethanol was evaporated by a rotavapor. Then 1N hydrochloric acid (4 eq) was added. After refluxing overnight the resulting product was precipitated. The mixture was extracted by ethyl acetate. The aqueous phase was modified to pH=4 by 1N of hydrochloric acid. The precipitate was filtered to obtain 9-anthryl alanine. 0.7 g of light yellow solid was obtained. The yield was 95%.

3. Synthesis of BoC-An-ala-OH

Diethyl (9-anthryl methyl) 2-[N-(tert-butoxycarbonyl) amino]malonate was mixed with 2 eq of sodium hydroxide in 10% water-ethanol solution, refluxing for four hours. Ethanol was evaporated. Then 2 eq of 1N hydrochloric acid was added slowly. The precipitate was filtered and dissolved in dioxane. After 5 hr of refluxing, the solvent was removed. The crude product was purified by column chromatography (Chloroform: methanol=9:1). 0.8 g of light yellow solid was obtained.

[$^1$H-NMR (chloroform-d) $\delta$1.12 (s, 9H, 3×CH$_3$), $\delta$3.93, 4.07 (m, 2H, CH$_2$), $\delta$4.26 (t, 1H, CH), $\delta$7.10 (s, 1, NH), δ7.52 (m, 4H, Ar-2, 3, 6, 7), 8.07 (m, 2H, Ar-1, 5), 8.44 (m, 2H, Ar-4,8), 8.49 (s, 1H, Ar-10)]

4. Synthesis of 9-Anthryl Alanine Methyl Ester 0.7 g of 9-anthryl alanine was mixed with 20 ml of anhydrous methanol, cooled to 0° C. 1.5 eq of thionyl chloride was added drop-wise, refluxing overnight. The solvent was removed on a rotary evaporator. The crude product was dissolved in ethyl acetate. The organic phase was washed by 5% of sodium bicarbonate, distilled water, and dried by anhydrous sodium carbonate. The solvent was removed on a rotary evaporator. The product was purified by column chromatography (hexane: ethyl acetate=1:2.5). 0.5 g of oil-like yellow solid was obtained. The yield was 68%. The product decomposes at 180° C.

[$^1$H-NMR(DMSO-d) δ1.62 (s, 2H, NH), δ3.63 (s, 3H, CH$_3$), 3.94, 4.10 (m, 2H, CH$_2$), δ4.15 (t, 1H, CH), δ7.50 (m, 2H, Ar-3, 7), δ7.57 (m, 2H, Ar-2, 6), 8.05 (m, 2H, Ar-4, 8), 8.35 (m, 2H, Ar-4,8), 8.43 (s, 1H, Ar-10)]

5. Synthesis of BOC-An-OMe 0.5 g of An-ala-OMe was dissolved in 5 ml of anhydrous DMF, and then 2 ml of trimethylamine was added. 0.6 g of (BOC)$_2$O was added with stirring at room temperature overnight. The solvent was removed. The crude product was washed with 5% of citric acid, extracted by ethyl acetate and dried by anhydrous sodium sulfate. The crude product was purified by column chromatography (hexane: ethyl acetate= 3:1). 0.5 g of yellow solid was formed. The yield was about 75%. The melting point is 190° C.

[$^1$H-NMR(chloroform-d) δ1.40 (s, 9H, 3×CH$_3$), δ3.33 (s, 3H, CH$_3$), δ4.07, 4.16 (m, 2H, CH$_2$), δ4.78 (t, H, CH), δ5.30 (s, 1, NH), δ7.50 (m, 2H, Ar-3, 7), 7.58 (m, 2H, Ar-2, 6), 8.03 (m, 2H, Ar-4, 8), 8.33 (m, 2H, Ar-1, 5), 8.43 (s, 1 H, Ar-10)]

Table 2 provides a key to the shorthand notation employed herein for various cyclic peptide structures.

TABLE 2

Key To Notation Abbreviations

| | |
|---|---|
| aib | aminoisobutyric acid |
| ala | alanine |
| an | anthracine |
| BOC | tert-butoxycarbonyl |
| Bzp | benzophenone |
| Bpa | Bzp |
| Fmoc | fluorenylmethoxycarbonyl |
| Nap | naphthalene |
| NMet | N-methyl |
| phe | phenanthrene |
| pya | pyrenylalanine |
| TFA | trifluoroacetic acid |

Solid Phase Peptide Synthesis

All resins, amino acids, and coupling reagents for solid phase peptide synthesis were purchased from Nova Biochem, and were used as received. All solvents and chemicals used in the synthesis of N-Fmoc-L-9-pyrenylalanine were purchased from Aldrich Chemicals, and were used as received. The enzymatic resolution of pyrenyl alanine was performed using aspergillus acylase enzyme, which was purchased from Tokyo Kasei Chemicals, and used as received. All solvents used for fluorescence measurements were spectrophotometric grade, purchased from Aldrich, and used as received.

The following methods were employed for peptide characterization:

a. Nuclear Magnetic Resonance. NMR spectra were obtained on a Bruker AVANCE 400 (400 MHz) spectrometer. Proton experiments were run at 400 MHz, and Carbon experiments at 100 MHz. Chemical shifts are reported in ppm (δ).

b. Infrared Spectroscopy. Infrared spectra were recorded on a Nexus 670 FT-IR in ATR mode. Bands are reported in wave numbers (cm$^{-1}$).

c. Fluorescence Spectroscopy. Fluorescence spectra were obtained on a Perkin-Elmer LS50-B spectrophotometer. Highly concentrated samples were measured in a 1 cm×0.2 cm quartz cell, and the reflected fluorescence measured to avoid observing internal absorption. For less concentrated samples, spectra were collected in a standard 1 cm×1 cm quartz fluorescence cell.

d. Mass-Spectrometry. Mass-spectral analysis was performed by the SynPep Corporation in Burbank, Calif. Spectra were obtained by electro-spray ionization with a carrier solvent of 1:1 H$_2$O:Acetonitrile and ultra-grade 5 nitrogen as a curtain gas.

e. Melting Points. Melting points were recorded on a Met-Temp melting point apparatus and are given uncorrected.

Synthesis of a Dipyrenyl Cyclic Peptide 1. 1-(Bromomethyl)pyrene.

A 10.00 g sample (43.1 mmol) of 1-Pyrenemethanol was dissolved in 250 mL of benzene with slight heating. The mixture was returned to room temperature and 1.63 mL (4.24 g, 17.24 mmol) of phosphorus tribromide were slowly added. The mixture was brought to reflux and stirred for 2 h. The mixture was returned to room temperature, and poured into a separatory funnel containing 500 mL 3:2 Et$_2$O:H$_2$O. The organic fraction was washed twice with 100 mL H$_2$O and dried over anhydrous Na$_2$SO$_4$. Solvent was removed under reduced pressure to yield 1-(bromomethyl) pyrene (12.030 g, 95.0%) as a dark yellow powder. TLC (SiO$_2$, 1:1 Hexane:EtOAc) Rf=0.95. Mp=270° C. (dec) $^1$H NMR (CDCl$_3$), δ 5.28 (s, 2H), 8.0–8.3 (m, 9H from pyrene). $^{13}$C NMR (CDCl$_3$), δ32.643, 123.258–132.374 16 pks from pyrene.

2. Diethyl-2-(1-pyrenylmethyl)-2-acetamidomalonate.

A 9.78 g (45.04 mmol) sample of diethyl acetamidomalonate, and 1.08 g sodium hydride (45.04 mmol) were suspended in 100 mL of anhydrous THF, under nitrogen, and at 0°C. After stirring for 5 min., 2.5 mL of anhydrous ethanol were added slowly, and the solution returned to room temperature. A solution of 1-(bromomethyl)pyrene (12.03 g, 40.9 mmol, dissolved in 100 mL dry THF) was slowly added to the reaction mixture, and the solution brought to reflux for 18 h. The bulk of the THF was removed under reduced pressure, and the remaining yellow slurry was dissolved in 400 mL 1:1 CH$_2$Cl$_2$:H$_2$O. The organic fraction was washed 3× with 100 mL H$_2$O, and dried over anhydrous Na$_2$SO$_4$. Solvent was removed under reduced pressure to produce Diethyl-2-(1-pyrenylmethyl)-2-acetamidomalonate (14.70 g, 83.1%) as a light yellow powder. TLC (SiO$_2$, 1:1 Hexane:EtOAc) Rf=0.57. Mp=135–140° C. $^1$H NMR (CDCl$_3$), δ1.37 (t, 6H), 1.95 (s, 3H), 3.76 (s, 2H), 4.30 (q, 6H), 6.42 (s, NH), 8.00–825 (m, 9H from pyrene).

3. N-Acetyl-DL-1-pyrenylalanine.

A 14.70 g sample (34.06 mmol) of Diethyl-2-(1-pyrenylmethyl)2-acetamidomalonate and 5.72 g (102.18 mmol) KOH were dissolved in 400 mL of 3:1 EtOH:H$_2$O, and the solution brought to reflux for 18 h. The solution was returned to room temperature and placed into a separatory funnel containing 250 mL CH$_2$Cl$_2$. The aqueous layer was extracted 3× with CH$_2$Cl$_2$ to remove unreacted starting material. The pH of the aqueous layer was adjusted to pH 2.0, and extracted 3× with 100 mL of CH$_2$Cl$_2$. The organic fraction was dried over anhydrous Na$_2$SO$_4$, and solvent removed under reduced pressure to produce N-Acetyl-DL-1-pyrenylalanine (12.40 g, 98.0%) as a light yellow powder. TLC (SiO$_2$, 8:1:0.5 CH$_2$Cl$_2$:MeOH:AcOH) R$f$0.45. Mp=215–218° C. MS (ESI) m/z [M+H]$^+$=332.2. (calc. 332.129)

4. L-1-pyrenylalanine.

A 12.40 g sample (27.25 mmol) of N-Acetyl-DL-1-pyrenylalanine was dissolved 300 mL of 3N NaOH. The pH of the solution was then adjusted to 7.5 with the careful addition of 6N HCl. Insoluble material was filtered off, and 1.94 g of aspergillus acylase was added to the solution, along with 0.030 g of CoCl$_2$.6H$_2$O to coordinate the enzyme. The resulting solution was agitated on an orbital shaker at 37° C. for 36 h, causing the precipitation of a fine white powder. The precipitate was isolated by centrifugation at 4000 rpm's for 15 min. The precipitate was washed with water to remove salts, and the product dried via lyophilization to give L-1-pyrenylalanine (5.19 g, 48%) as an off-white solid. TLC (SiO$_2$, 8:1:0.5 CH$_2$Cl$_2$:MeOH:AcOH) R$f$=0.73 Mp=205–210° C. MS (ESI) m/z [M+H]$^+$=290.2 (calc. 290.118).

5. N-Fmoc-L-1-pyrenylalanine.

A 5.19 g sample (17.90 mmol) of L-1-pyrenylalanine was suspended in 70 mL of dioxane, along with 6.64 g (19.69 mmol) of 9-Fluorenylmethyloxycarbonyl-N-hydroxysuccinimide (Fmoc-Osu), and 5.79 mL (4.30 g, 35.8 mmol) of diisopropylethylamine. The mixture was stirred for 24 h, and unreacted L-1-pyrenylalanine filtered from the mixture. The filtrate was acidified to a pH of 2 with 1N HCl, and dioxane removed with rotary evaporation. The resulting precipitate was filtered, and recrystallized from THF:Heptane to obtain N-Fmoc-L-1-pyrenylalanine as a tan powder. The product was further purified over normal phase silica gel with 10:1 CH$_2$Cl$_2$:MeOH as the mobile phase to give 4.39 g (48%) of the pure product. TLC (SiO$_2$ 17:1 CH$_2$Cl$_2$:MeOH) R$f$=0.23. Mp=186–190° C. $^1$H NMR (DMSO), δ3.50, 3.87 (dd, 2H), 4.03 (m, 3H, overlap of chiral CH and Fmoc CH$_2$), 4.34 (m, 1H, fluorene bridgehead), 7.05–8.22 (m, 18H, pyrene and fluorene Ar—H). MS (ESI) m/z [M +Na]$^+$=534.0 (calc. 534.168), [M+K]$^+$=550.0 (calc. 550.276)

6. Linear peptide lin[-aib-pya-aib-phe-]$_2$.

Lin[-aib-pya-aib-phe-]$_2$ was synthesized via solid phase peptide synthesis in a 65% overall yield relative to the resin loading. Crude linear peptide was purified by flash column chromatography on silica gel with 17:1 CH$_2$Cl$_2$:MeOH as the mobile phase. Peptide purity was assessed using reverse phase HPLC with 6:4 CH$_3$CN:0.1% TFA as the mobile phase. Mp =158–162° C. MS (ESI) m/z [M+H]$^+$=1195.4 (calc 1195.566)

7. Cyclic peptide cyclo[-aib-pya-aib-phe-]$_2$.

Cyclo[-aib-pya-aib-phe-]$_2$ was produced by solution phase cyclization of its linear analogue, using HATU and HOAT as coupling reagents, with 10 eq of DIEA as a base, in DMF. The crude cyclic product was purified in a similar fashion to its linear counterpart. Peptide purity was again assessed using reverse phase HPLC. Mp=165–168° C. MS (ESI) m/z [M+H]$^+$=1177.6 (calc. 1177.556), [M+Na]$^+$= 1199.8 (calc 1199.538).

8. Linear peptide lin[-ala-pya-ala-phe-]$_2$.

Lin[-ala-pya-ala-phe-]$_2$ was synthesized in the same fashion as described above for the other linear peptide, and was purified by similar means. Mp=170–175° C. MS (ESI) m/z [M+H]$^+$=1139.6 (calc.1139.504) IR (ATR): Amide I band: 1629 cm$^{-1}$, Amide II band: 1529.27.

9. Cyclic Peptide cyclo[-ala-pya-ala-phe-]$_2$.

Cyclo[-ala-pya-ala-phe-]$_2$ was produced by solution phase cyclization of its linear analogue with the same coupling reagents as described earlier. Purification was performed with the same techniques as for the other cyclic peptide. Mp=178–180° C. MS (ESI) m/z [M+K]$^+$=1159.6 (calc. 1159.583) IR (ATR): Amide I band 1626.25 cm$^{-1}$, Amide II band: 1512.39, 1504.36

Figure 10A:
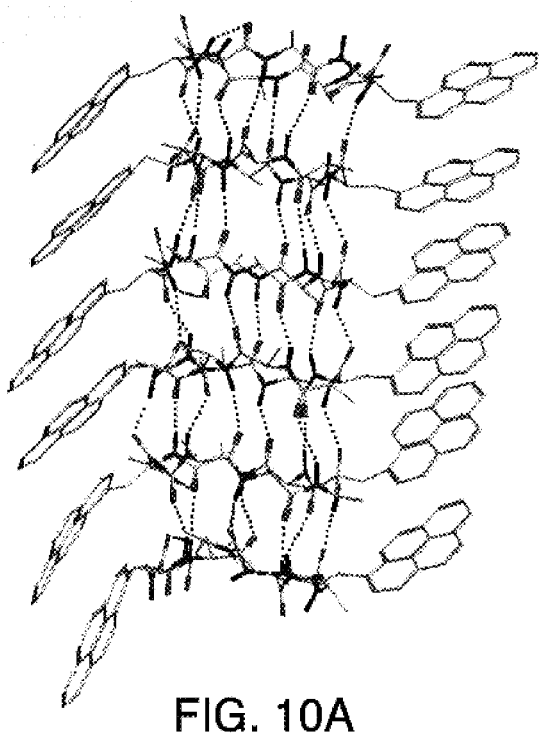
FIGS. 10A and 10B show a molecular model of a six layer di-pyreneyl cyclic peptide nanotube with parallel stacking (FIG. 10A) and the preferred anti-parallel stacking (FIG. 10B)
Figure 10B:
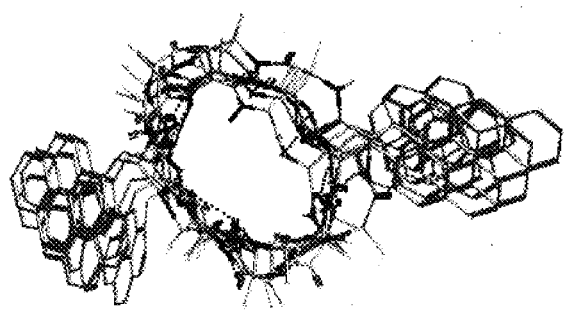

FIGS. 10A and 10B show a molecular model of a cyclic peptide nanotube formed from the synthesized dipyrenyl cyclic peptide. Parallel stacking of the cyclic peptide is shown in FIG. 10A while anti-parallel stacking is shown in FIG. 10B. For the sake of simplicity, FIGS. 10A and 10B show only six stacked cyclic peptides forming a cyclic peptide nanotube structure. It is important to note that cyclic peptide nanotube structures ranging from a monolayer to 2000 layers are possible.

Synthesis of a Tetrapyrenyl Cyclic Peptide

Figure 17:
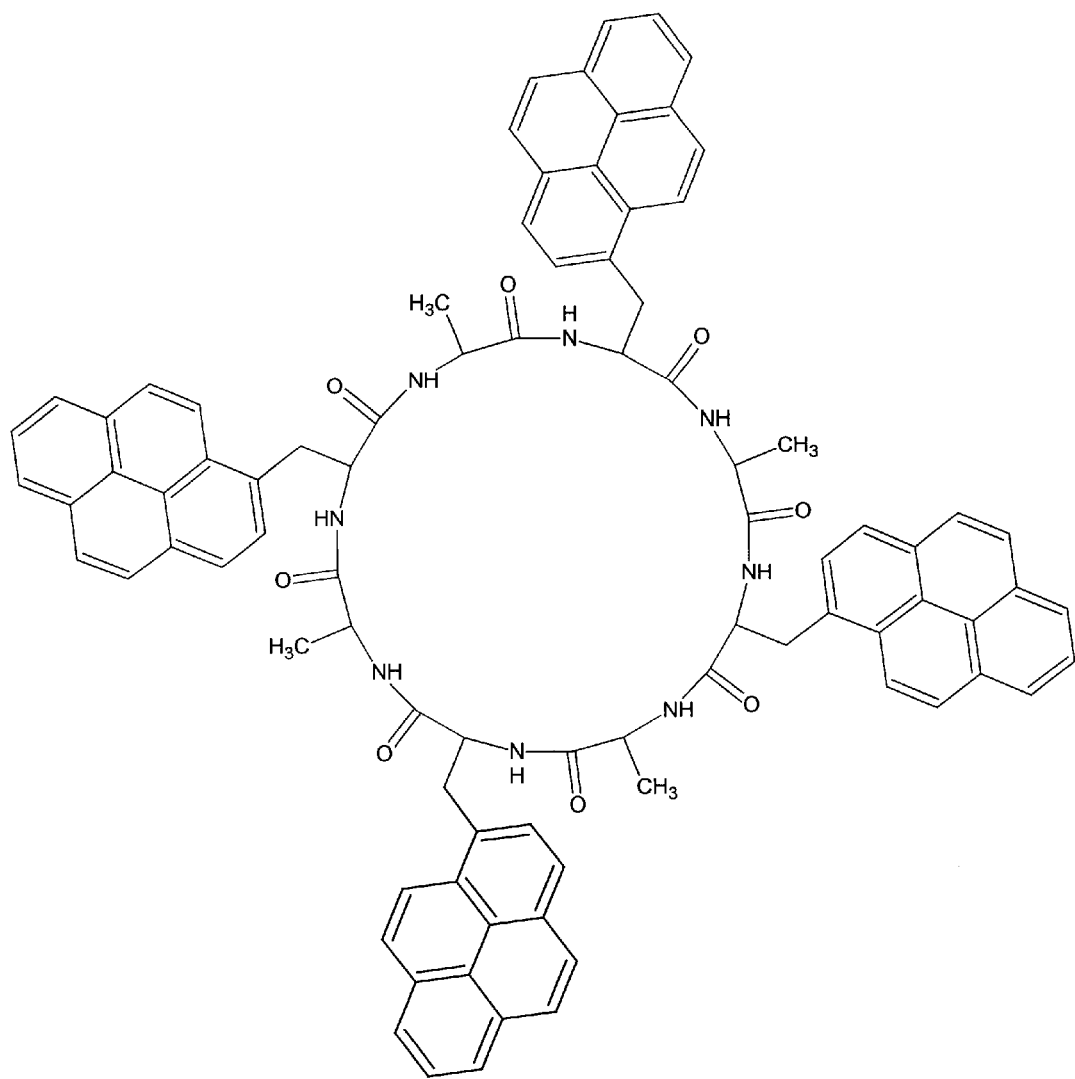
FIG. 17 shows one embodiment of tetra-pyreneyl cyclic peptide of the present invention.

The proposed tetrapyrenyl structure consists of this linear sequence of amino acids that is cyclized end-to-end (Ala-Pya-Ala-Pya-Ala-Pya-Ala-Pya). A schematic of a tetrapyrenyl cyclic peptide is shown in FIG. 17. The sequence shown is an example and may include other amino acids in place of Ala. The reason for constructing this peptide is as follows. In the di-pyrenyl molecule already synthesized, anti-parallel stacking of the peptides, which is the normal way that stacking occurs to form nanotubes, can occur with the pyrene groups of adjacent cyclic peptides in the nanotube lining up in a face-to-face arrangement. It is this pyrene-pyrene alignment that we are claiming can provide extended conduction of electrons along the nanotube. However, anti-parallel stacking can also potentially lead to a staggered arrangement of pyrene groups where they are not arranged face-to-face. If such is the case, electron conduction will be less efficient.

It is one of our contentions that the π—π interaction that occurs when pyrene and other aromatic groups are arranged face-to-face provides a driving force for the cyclic peptides to stack with a face-to-face arrangement. Certainly, previous work with pyrene crystals and pyrene in solution attests to the energetic favorability of such a face-to-face arrangement. Our results to date with the di-pyrenyl system support the conclusion that there is significant face-to-face interactions. However, in order to maximize the extent of such an interaction, it is our intention to synthesize a cyclic peptide containing 4 pyrene chromophores arranged alternately in the peptide. This is expected to increase the likelihood of π—π stacking in two ways. First, statistically there will be a greater probability of peptides stacking in such a face-to-face conformation. Secondly, there will be a greater driving force provided by the larger number of pyrenes present. Depending on the results obtained, the number of pyrene groups incorporated into the peptide structure may be adjusted for maximum face-to-face overlap.

The synthesis of cyclic peptides containing differing numbers of pyrene groups follow the general procedures described for the synthesis of the di-pyrenyl molecule already synthesized. This procedure involves the synthesis of enantiomerically-pure pyrenylalanine by the procedures described, the growth of a linear peptide containing the desired number of pyrenyl alanines by solid phase techniques, cleavage of the linear peptide from the solid support, such as a polystyrene resin, conversion of the C-terminus of the peptide from a carboxylic acid to a reactive group, such as an acid chloride, and cyclization. Spectroscopic determinations, for example UV-visible absorption spectroscopy, fluorescence spectroscopy and time resolved fluorescence and absorption techniques, may be used along with scanning probe microscopy to confirm the presence of cyclic peptides, cyclic peptide nanotubes and their conformation vis a vis the arrangement of pyrene groups.

We note that the use of pyrene as the electroactive group in the cyclic peptide nanotube is not necessary. Other aromatic groups or aromatic ketones may also be used to provide the electron conduction capability foreseen for the pyrene groups. For other groups, synthetic and characterization procedures similar to those described above or those found in the literature may be used. The key point is that the cyclic peptide nanotube is being used as structural scaffold to which electroactive groups can be appended in a rational way. We note that the electroactive groups are not appended to the peptide or the peptide nanotube after the synthesis of these structures but rather they are incorporated into the peptide as appended groups during the synthesis of the peptide itself.

Electrical conduction in cyclic peptide nanotubes containing pyrene or other electroactive groups and the electrical application of such nanotubes may be achieved by the deposition of cyclic peptide nanotubes as monolayers on conducting or semiconducting surfaces by chemical adsorption or by forming covalent links between the surface and the nanotube. An example of forming a self-assembled monolayer of cyclic peptides nanotubes on a gold surface is provided below. We note that covalently linking nanotubes to other surfaces, such as silicon and silica, can also be achieved through the functional groups on amino acid side chains or through functional groups that can be attached to amino acid side chains by standard synthetic procedures.

Molecules containing sulfur groups such as thiols and disulfides are known to form ordered self-assembled monolayers on metals such as gold. One strategy that may be used is the incorporation of sulfur-containing natural amino acids such as cysteine or methionine into the cyclic peptide backbone that contains the desired electroactive groups. Alternatively, amino acids can be synthesized which contain alkylthiol side chains and then incorporated into the cyclic peptide structure. Such cyclic peptides are capable of self assembling on metallic surfaces such as gold. Depending on the kinetics of cyclic peptide stacking, cyclization of individual peptides may either be performed with the gold surface in situ or separately followed by introduction of the gold surface. It is our expectation that the cyclic peptide nanotubes may self-assemble with the long axis of the nanotube perpendicular to the gold surface or at some angle greater than approximately 45° to the surface. It is possible to determine the conductivity of peptide nanotubes by using the tip of a scanning tunneling microscope or a conducting atomic force microscope to measure the current as a function of voltage applied across the tip and conducting surface.

Applications of Cyclic Peptides and Cyclic Peptide Nanotubes

The incorporation of a conducting cyclic peptide nanotube into a molecular electronic device can potentially be achieved by a number of methods. One potential method is the self-assembly of a cyclic peptide nanotube monolayer on gold followed by chemical vapor deposition of gold or some other method of depositing gold on top of the monolayer to produce two metallic surfaces sandwiching the nanotube monolayer.

In addition to electronic conduction applications, cyclic peptide nanotube supramolecular assemblies containing alternating electron donor-electron acceptor groups may provide for a family of materials having precisely controlled non-linear optical behavior.

Optical sensors offer another promising application for cyclic peptide nanotube supramolecular assemblies which comprise appended chromoionophore groups. As noted above, in these applications the cyclic peptide nanotubes act as structural scaffolds to which useful groups can be appended. In this particular application, chromoionophore groups that are capable of selectively binding a species of interest and optically signaling the binding event may be appended to nanotube scaffold structures. The chromoionophore is a molecule that contains both an ion binding or complexation site and a chromophore or light absorbing/emitting group whose optical properties are sensitive to the presence of a complexed ion. Two examples of chromoionophore applications are provided below.

In one example chromoionophore application, such structures may be employed for the detection of sodium ions in aqueous-based media. Sodium ions are an important analyte in human blood and their detection and quantification is important for clinical diagnosis of disease. Peptides may be synthesized which contain an amino acid that has a chromoionophore group appended to it. The amino acid could be an alanine or any of a variety of naturally-occurring amino acids, but one attractive option is the use of an amino acid with a reactive side chain, i.e., a side chain that can be functionalized. Lysine is one such example. Through standard synthetic techniques it is possible to incorporate a wide variety of chromoionophore structures that have been previously proven to be effective in bulk optode applications, for example, in bulk polymer membranes.

One chromoionophore that may be used is an azacrown ether that is attached through the nitrogen atom in the crown structure to a fluorescent chromophore. Azacrown ethers have been shown previously to complex a variety of alkali metal ions. The mode of complexation is electrostatic stabilization of the ions in a binding pocket formed by the oxygen atoms in the azacrown structure. The operation of this chromoionophore is characterized as an 'off-on' switch. In the absence of complexed ion, the nitrogen atom in the azacrown structure quenches the excited state of the chromophore by internal electron transfer leading to non-emissive behavior. In the presence of complexed ion, the electrostatic field of the ion disrupts the internal electron transfer process leading to emission from the chromophore. The concentration of ions is directly proportional to the emission intensity. Many other examples of chromoionophore sensors have been published and many of their structures are amenable to synthetic incorporation into cyclic peptides.

In another example chromoionophore application, the cyclic peptide nanotube may be employed as a molecular scaffold for a 'collective response' optical sensor. It is well known that excitation energy can migrate rapidly as excitons through conjugated systems such as polymers and that defect sites or energy sinks in the polymer can trap this energy. Swager describes the effect of a benzo-crown ether binding site appended to the backbone of a polyacetylene [see T. M. Swager, Accounts of Chemical Research, 31:201 (1998)]. In this example, the binding is selective for paraquat. In the absence of paraquat, photoexcitation of the polymer results in fluorescence emission. However, binding paraquat introduces an energy sink into the polymer. Exciton migration to the binding site triggers an electron transfer process to paraquat, destruction of the exciton and fluorescence quenching. In theory, as long as the polymer is conjugated, thereby allowing free flow of the excitons, only one binding event is necessary to cause an effect that can be measured, presenting the opportunity for very high sensitivity. Similar exciton migration can occur 'through-space' rather than through a conjugated system such as the polyacetylene described above, particularly if there is face-to-face overlap of π orbitals such as is found in pyrene-containing cyclic peptide nanotubes of the present invention. Thus, the same electron conduit that is asserted for face-to-face stacked pyrenes in nanotubes can also act as an efficient conduit for excitons. By way of example, cyclic peptide nanotube collective response sensors that possess the following characteristics are particularly useful:

1. A fluorescent exciton conduit provided by groups that are attached to each individual cyclic peptide molecule in the nanotube:

An example of such a conduit would be the face-to-face alignment of pyrene groups as described above for the electronic conduction application, or it could be provided by other groups that yield the same effect. The groups that make up the conduit will have fluorescence yields that are sensitive to the presence of analytes. For example, the group that provides the exciton conduit may have fluorescence yields sensitive to ions or other redox active groups. The synthesis of the amino acid residues containing these exciton conduit groups would be carried out by standard techniques already described.

2. A binding site or complexation site in each individual cyclic peptide that is physically close to the groups that form the exciton conduit:

Such a binding site could be attached covalently to the same amino acid residue as the group that provides the exciton conduit or it could be attached to an adjacent residue that allows the exciton conduit and the binding site to be in close proximity to each other. An example of a binding site would be the benzocrown ether described by Swager (see above) that is able to complex paraquat. This is only one example since, essentially, a binding site for any analyte that is capable of affecting the fluorescence of the exciton conduit groups can be used.

The advantages of using cyclic peptide nanotubes as scaffolds for these chromoionophores are manifold. First, the peptide nanotube structure will provide a higher density of chromoionophore sites than in typical bulk optical sensors in which the sensor molecules are dispersed in a polymer membrane. Second, since all of the sensor sites are present at the surface of the nanotube, there is a much higher density of usable chromoionophore sites that do not require significant diffusional motion of the analyte through a polymer membrane in order to operate. This also will substantially decrease the response time of the sensor, an important consideration in sensors required in commercial applications. Third, the natural affinity of cyclic peptide nanotube sensors for lipid membranes presents the opportunity to use these structures as in situ sensors for the movement of analytes through cell membranes.

Other applications exist for cyclic peptides containing redox-active chromophores to produce a molecular scale magnet. Some initial experiments have shows that positive charge can be introduced photochemically onto a chromophore in a cyclic peptide. In one example, a cyclic peptide was synthesized that contains benzophenone and N-ethylcarbazole groups at residue positions 2 and 6 in the following residue sequence cyclo-[aib-cbz-aib-phe-aib-bzp-aib-phe] where "aib" is α-amino-iso-butyric acid, "cbz" is N-ethylcarbazolylalanine, "phe" is phenylalanine and "bzp" is 4-phenyl-benzoylalanine. Here, the point of attachment on the carbazole is at the 3-position. This position was chosen for synthetic ease. While there are many other possible amino acid sequences that could be used, the presence of "aib" is important because it prevents stacking of the peptides. It is important for this application to have monomeric units since stacked cyclic peptides would promote inter-peptide charge transfer that would interfere with the intra-peptide charge transfer necessary for the device function. We have studied the photophysics of this cyclic peptide and have found that there is a high yield for photoionization of the carbazole chromophore following excitation at 355 nm with a pulsed Nd/YAG laser. This result proves that charge can be introduced to a chromophore on a cyclic peptide photochemically. In addition, the intense absorption of the carbazole cation radical enables photoexcitation of the carbazole which can produce the transfer of charge to another chromophore. Support for this suggestion comes from previous work as outlined above and also from unpublished work on energy transfer in individual cyclic peptide molecules. This work has shown that triplet excitation energy can be transferred rapidly, in response to an energy gradient, from one chromophore to another in a cyclic peptide molecule. Since triplet-triplet energy transfer occurs by an electron exchange mechanism similar to charge transfer, this is a relevant analogy for the charge transfer process proposed herein. Research on triplet energy and charge transfer in helical acyclic peptides also supports the concept of charge transfer in peptides.

Having described the preferred embodiments of the invention, it will now become apparent to one of skill in the art that other embodiments incorporating the disclosed concept may be used. Therefore, it is not intended to limit the invention to the disclosed embodiment but rather the invention should be limited only by the spirit and scope of the following claims.

What is claimed is:

1. A stackable cyclic peptide having the following general formula:

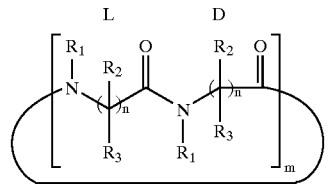

wherein $R_1$ is H, $CH_3$ or alkyl;

wherein $R_2$ is a chromophore;

wherein $R_3$ is H, $CH_3$ or a polar or non-polar organic functional group used for controlling peptide stacking and solubility;

wherein n equals 1 or 2;

wherein m equals 4 or 6; and wherein a first adjacent amino acid residue has an α-carbon chirality of L and a second adjacent amino acid residue has an α-carbon chirality of D.

* * * * *